United States Patent
Hwang et al.

(10) Patent No.: US 10,074,808 B2
(45) Date of Patent: Sep. 11, 2018

(54) CONDENSED CYCLIC COMPOUND AND ORGANIC LIGHT-EMITTING DEVICE INCLUDING THE SAME

(71) Applicants: SAMSUNG DISPLAY CO., LTD., Yongin, Gyeonggi-Do (KR); Research & Business Foundation SUNGKYUNKWAN UNIVERSITY, Suwon, Gyeonggi-do (KR)

(72) Inventors: Jinsoo Hwang, Yongin (KR); Myeongsuk Kim, Yongin (KR); Sungwook Kim, Yongin (KR); Seungsoo Yoon, Suwon (KR)

(73) Assignees: SAMSUNG DISPLAY CO., LTD., Yongin, Gyeonggi-do (KR); Research & Business Foundation SUNGKYUNKWAN UNIVERSITY, Suwon, Gyeonggi-do (KR)

( * ) Notice: Subject to any disclaimer, the term of this patent is extended or adjusted under 35 U.S.C. 154(b) by 314 days.

(21) Appl. No.: 14/656,018

(22) Filed: Mar. 12, 2015

(65) Prior Publication Data
US 2016/0049590 A1    Feb. 18, 2016

(30) Foreign Application Priority Data
Aug. 14, 2014    (KR) .................. 10-2014-0106221

(51) Int. Cl.
*H01L 51/00* (2006.01)
*C07C 13/28* (2006.01)
(Continued)

(52) U.S. Cl.
CPC .......... *H01L 51/0058* (2013.01); *C07C 13/62* (2013.01); *C07C 2603/24* (2017.05);
(Continued)

(58) Field of Classification Search
CPC ...... H01L 51/0052; C07C 13/62; C07C 13/72
See application file for complete search history.

(56) References Cited

U.S. PATENT DOCUMENTS 8,395,144 B2 *  3/2013  Lee .................. C07C 13/62
                                        257/40
9,525,138 B2 * 12/2016  Moon ............... H01L 51/0052
(Continued)

FOREIGN PATENT DOCUMENTS

KR    10-2010-0017136 A    2/2010
KR    10-2010-0027950 A    3/2010
(Continued)

*Primary Examiner* — Rip A Lee
(74) *Attorney, Agent, or Firm* — Lee & Morse, P.C.

(57) ABSTRACT

A condensed cyclic compound and an organic light-emitting device, the compound being represented by Formula 1 below:

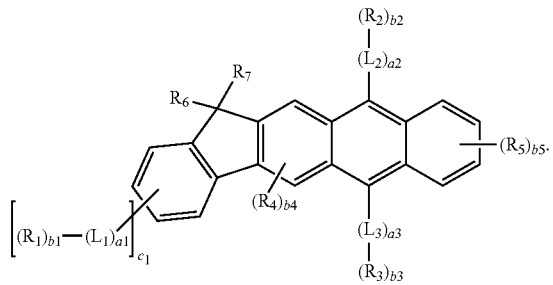

12 Claims, 1 Drawing Sheet

(51) Int. Cl.
  *C07C 13/62*   (2006.01)
  *H01L 51/50*   (2006.01)
(52) U.S. Cl.
  CPC ...... *C07C 2603/48* (2017.05); *C07C 2603/50* (2017.05); *C07C 2603/52* (2017.05); *C07C 2603/94* (2017.05); *H01L 51/0055* (2013.01); *H01L 51/0077* (2013.01); *H01L 51/0081* (2013.01); *H01L 51/0085* (2013.01); *H01L 51/5012* (2013.01); *H01L 51/5016* (2013.01); *H01L 2251/308* (2013.01)

(56) References Cited

U.S. PATENT DOCUMENTS

| | | |
|---|---|---|
| 2008/0315754 A1 | 12/2008 | Kawamura et al. |
| 2010/0140604 A1 | 6/2010 | Yamada et al. |
| 2011/0210320 A1 | 9/2011 | Shin et al. |
| 2012/0097924 A1 | 4/2012 | Kim et al. |
| 2014/0103306 A1* | 4/2014 | Moon ................ H01L 51/0052 257/40 |

FOREIGN PATENT DOCUMENTS

| | | | | |
|---|---|---|---|---|
| KR | 10-2010-0067062 A | 6/2010 | | |
| KR | 10-2010-0137243 A | 12/2010 | | |
| KR | 10-2011-0081698 A | 7/2011 | | |
| KR | 10-2012-0043623 A | 5/2012 | | |
| WO | WO 2009/139580 A2 * | 11/2009 | ........... | C07D 333/76 |
| WO | WO 2010/110554 A2 * | 9/2010 | ............. | C09K 11/06 |

* cited by examiner

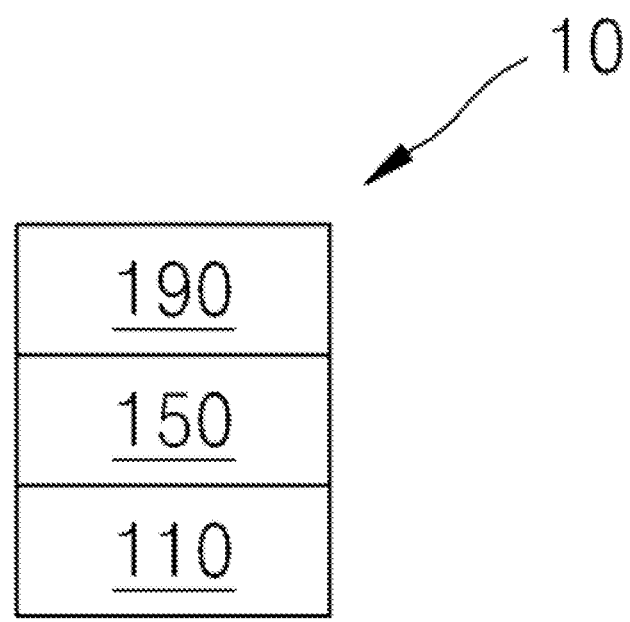

CONDENSED CYCLIC COMPOUND AND ORGANIC LIGHT-EMITTING DEVICE INCLUDING THE SAME

CROSS-REFERENCE TO RELATED APPLICATION

Korean Patent Application No. 10-2014-0106221, filed on Aug. 14, 2014, in the Korean Intellectual Property Office, and entitled: "Condensed Cyclic Compound and Organic Light-Emitting Device Including the Same," is incorporated by reference herein in its entirety.

BACKGROUND

1. Field

Embodiments relate to a condensed cyclic compound and an organic light-emitting device including the same.

2. Description of the Related Art

Organic light emitting devices are self-emission devices that have wide viewing angles, high contrast ratios, short response times, and excellent brightness, driving voltage, and response speed characteristics, and produce full-color images.

The organic light-emitting device may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, e.g., holes and electrons, may be recombined in the emission layer to produce excitons. These excitons change from an excited state to a ground state, thereby generating light.

SUMMARY

Embodiments are directed to a condensed cyclic compound and an organic light-emitting device including the same.

One or more embodiments relate to a condensed cyclic compound and an organic light-emitting device including the same.

An aspect of an exemplary embodiment provides a condensed cyclic compound represented by Formula 1 below:

<Formula 1>

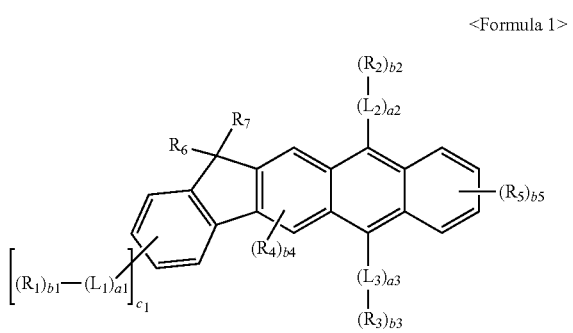

wherein in Formula 1, $L_1$ to $L_3$ may be each independently selected from a substituted or unsubstituted $C_3$-$C_{10}$ cycloalkylene group, a substituted or unsubstituted $C_3$-$C_{10}$ cycloalkenylene group, a substituted or unsubstituted $C_6$-$C_{60}$ arylene group, and a substituted or unsubstituted divalent non-aromatic condensed polycyclic group;

a1 may be selected from 1, 2, and 3;

a2 and a3 may be each independently selected from 0, 1, 2, and 3;

$R_1$ to $R_7$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group (substituted or unsubstituted monovalent non-aromatic condensed polycyclic group), —N($Q_1$)($Q_2$), —Si($Q_3$)($Q_4$)($Q_5$), and —B($Q_6$)($Q_7$);

$R_6$ and $R_7$ may be separate or be linked to each other to form a saturated or unsaturated ring, b1 to b5 may be each independently an integer selected from 1, 2, and 3;

c1 is an integer selected from 1, 2, 3, and 4;

at least one substituent of the substituted $C_3$-$C_{10}$ cycloalkylene group, substituted $C_3$-$C_{10}$ cycloalkenylene group, substituted $C_6$-$C_{60}$ arylene group, substituted a divalent non-aromatic condensed polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_6$-$C_{60}$ aryl group, substituted $C_6$-$C_{60}$ aryloxy group, substituted $C_6$-$C_{60}$ arylthio group, and substituted monovalent non-aromatic condensed polycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, and a monovalent non-aromatic condensed polycyclic group;

a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, and a monovalent non-aromatic condensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_6$-$C_{60}$ aryl group, and a monovalent non-aromatic condensed polycyclic group.

An aspect of another exemplary embodiment provides an organic light-emitting device includes: a first electrode; a second electrode facing the first electrode; and an organic layer that is disposed between the first electrode and the second electrode and includes an emission layer, wherein the organic layer includes at least one of the condensed cyclic compound described above.

BRIEF DESCRIPTION OF THE DRAWING

Features will be apparent to those of skill in the art by describing in detail exemplary embodiments with reference to the attached drawing in which:

FIG. 1 illustrates a schematic view of an organic light-emitting device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list.

A condensed cyclic compound according to an embodiment may be represented by Formula 1 below:

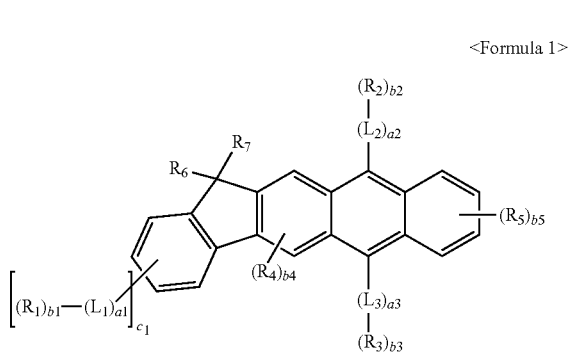

<Formula 1>

In Formula 1, $L_1$ to $L_3$ may each independently be selected from a substituted or unsubstituted $C_3$-$C_{10}$ cycloalkylene group, a substituted or unsubstituted $C_3$-$C_{10}$ cycloalkenylene group, a substituted or unsubstituted $C_6$-$C_{60}$ arylene group, and a substituted or unsubstituted divalent non-aromatic condensed polycyclic group.

For example, $L_1$ to $L_3$ in Formula 1 may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, and an ovalenylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, and an ovalenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group.

In an implementation, $L_1$ to $L_3$ may each independently be selected from a group represented by one of Formulae 3-1 to 3-13 below:

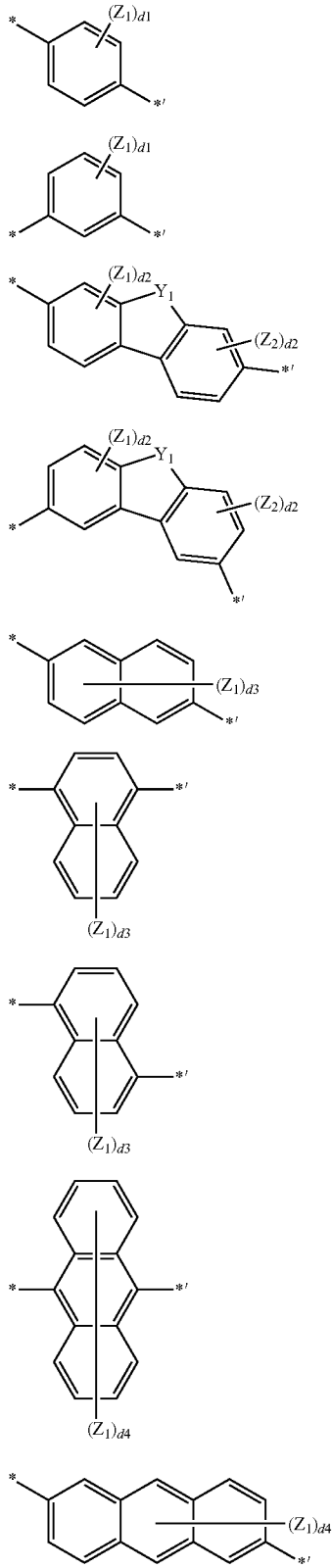

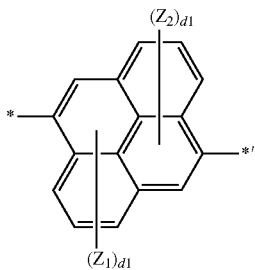

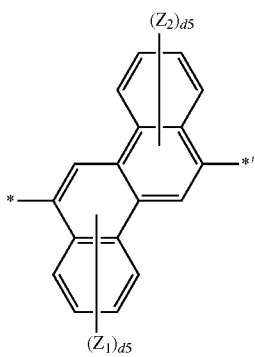

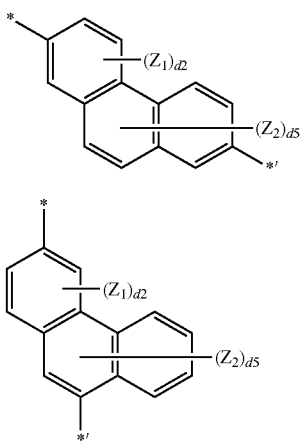

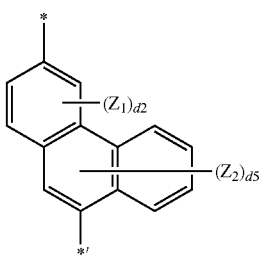

In Formulae 3-1 to 3-13, $Y_1$ may be $C(Z_3)(Z_4)$;

$Z_1$ to $Z_4$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, d1 may be an integer selected from 1, 2, 3, and 4, d2 may be an integer selected from 1, 2, and 3, d3 may be an integer selected from 1, 2, 3, 4, 5, and 6, d4 may be an integer selected from 1, 2, 3, 4, 5, 6, 7, and 8, d5 may be an integer selected from 1, 2, 3, 4, and 5, and * and *' indicate binding sites to a neighboring atom.

In an implementation, $L_1$ to $L_3$ may each independently be selected from a group represented by one of Formulae 4-1 to 4-15 below.

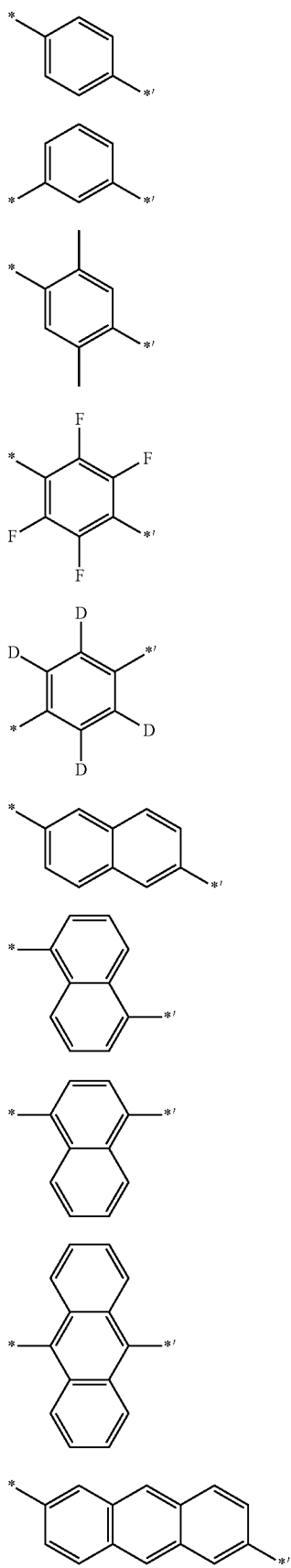
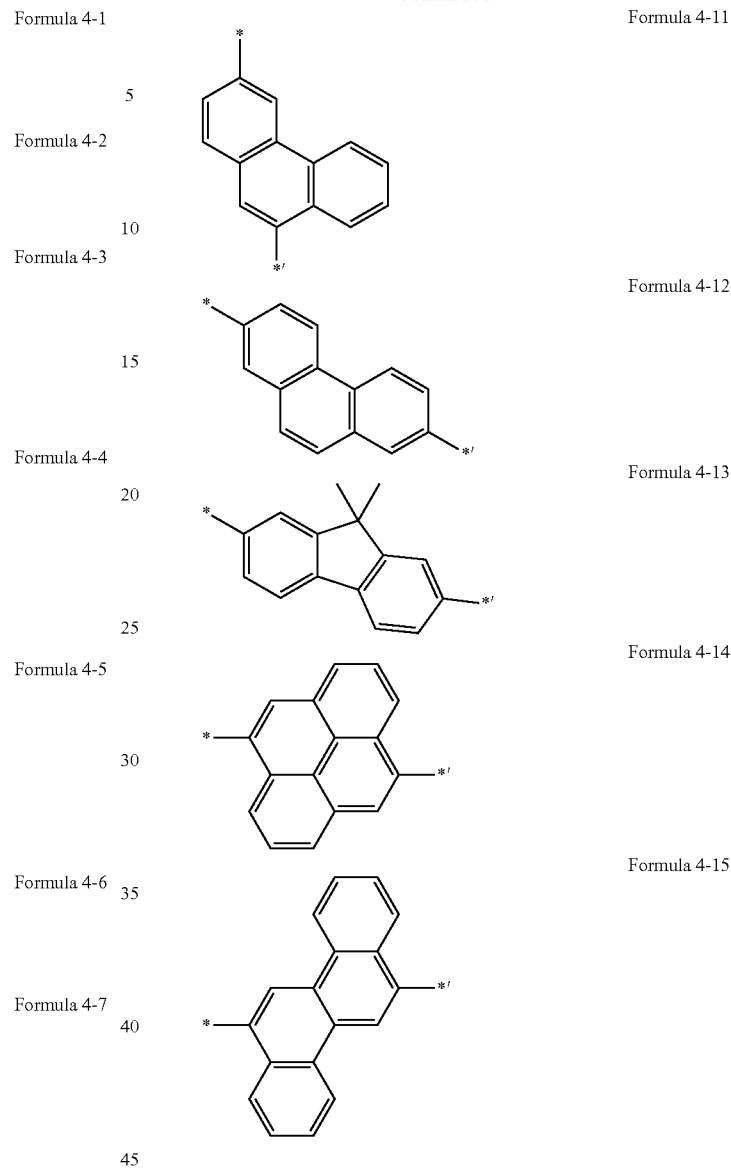

*and *' in Formulae 4-1 to 4-15 indicate binding sites to a neighboring atom.

In Formula 1, a1 indicates the number of $L_1$, a2 indicates the number of $L_2$, and a3 indicates the number of $L_3$. For example, a1 may be an integer selected from 1, 2, and 3, and a2 and a3 may each independently be an integer selected from 0, 1, 2, and 3.

When a2 or a3 is 0, *-$(L_2)_{a2}$-*' or *-$(L_3)_{a3}$-*' may be a single bond. When a1, a2, or a3 is 2 or more, a plurality of $L_1$ may be identical or different, a plurality of $L_2$ may be identical or different, and a plurality of $L_3$ may be identical or different.

In an implementation, in Formula 1, a1 may be 1, and a2 and a3 may each independently be 0 or 1.

$R_1$ to $R_7$ in Formula 1 may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group, —N($Q_1$)($Q_2$), —Si($Q_3$)($Q_4$)($Q_5$), and —B($Q_6$)($Q_7$).

In an implementation, $R_1$ to $R_5$ in Formula 1 may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted monovalent non-aromatic condensed polycyclic group, and —Si($Q_3$)($Q_4$)($Q_5$), and $R_6$ and $R_7$ may each independently be selected from a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, and a substituted or unsubstituted monovalent non-aromatic condensed polycyclic group.

In an implementation, $R_1$ to $R_5$ may each independently be selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group; and Si($Q_3$)($Q_4$)($Q_5$) (wherein $Q_3$ to $Q_5$ are each independently selected from a $C_1$-$C_{20}$ alkyl group, a $C_1$-$C_{20}$ alkoxy group, a phenyl group, and a naphthyl group).

In an implementation, $R_1$ to $R_5$ may each independently be selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid and a salt thereof, a $C_1$-$C_{20}$ alkyl group, and a $C_1$-$C_{20}$ alkoxyl group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, and a chrysenyl group.

$R_6$ and $R_7$ in Formula 1 may each independently be selected from:

a $C_1$-$C_{20}$ alkyl group and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, and a chrysenyl group.

In an implementation, $R_1$ to $R_5$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid and a salt thereof, a $C_1$-$C_{20}$ alkyl group, a $C_1$-$C_{20}$ alkoxyl group, and a group represented by one of Formulae 5-1 to 5-11 below.

In an implementation, $R_6$ and $R_7$ may each independently be selected from a $C_1$-$C_{20}$ alkyl group, a $C_1$-$C_{20}$ alkoxy group, and a group represented by one of Formulae 5-1 to 5-11 below.

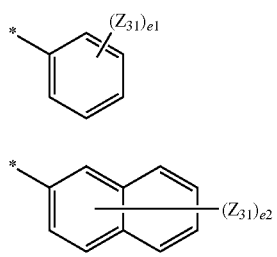

Formula 5-1

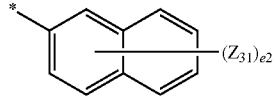

Formula 5-2

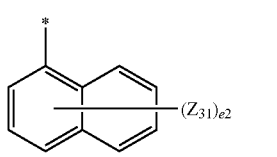

Formula 5-3

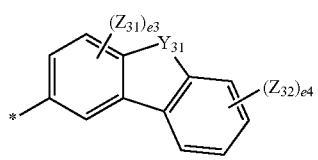

Formula 5-4

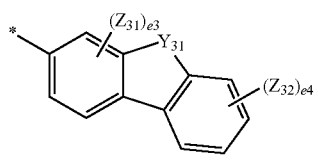

Formula 5-5

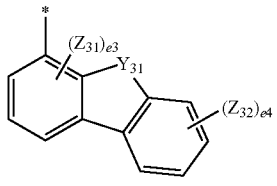

Formula 5-6

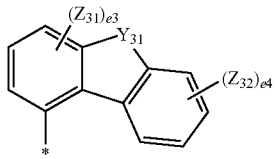

Formula 5-7

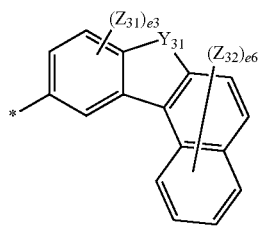

Formula 5-8

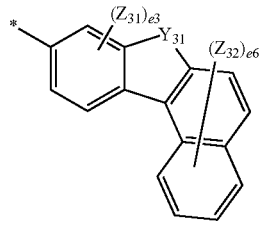

Formula 5-9

Formula 5-10

Formula 5-11

In Formulae 5-1 to 5-11, $Y_{31}$ may be $C(Z_{33})(Z_{34})$;

$Z_{31}$ to $Z_{34}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzo-fluorenyl group, a dibenzofluorenyl group, a phenanthrenyl group, an anthracenyl group, a pyrenyl group, and a chrysenyl group, e1 may be an integer selected from 1, 2, 3, 4, and 5, e2 may be an integer selected from 1, 2, 3, 4, 5, 6, and 7, e3 may be an integer selected from 1, 2, and 3, e4 may be an integer selected from 1, 2, 3, and 4, e5 may be an integer selected from 1, 2, 3, 4, and 5, e6 may be an integer selected from 1, 2, 3, 4, 5, and 6, and * indicates a binding site to a neighboring atom.

In an implementation, $R_1$ to $R_5$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid and a salt thereof, a $C_1$-$C_{20}$ alkyl group, a $C_1$-$C_{20}$ alkoxyl group, and a group represented by one of Formulae 6-1 to 6-18 below.

In an implementation, $R_6$ and $R_7$ may each independently be selected from a $C_1$-$C_{20}$ alkyl group, a $C_1$-$C_{20}$ alkoxy group, and a group represented by one of Formulae 6-1 to 6-18 below.

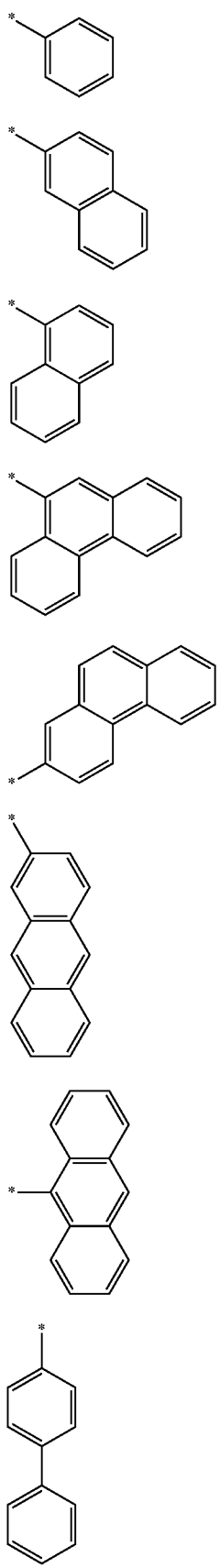
Formula 6-1
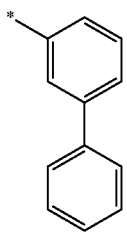
Formula 6-2
Formula 6-3
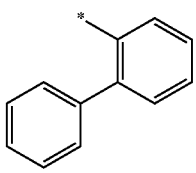
Formula 6-4
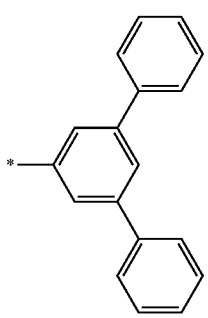
Formula 6-5
Formula 6-6
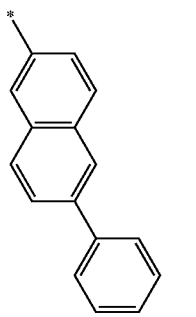
Formula 6-7
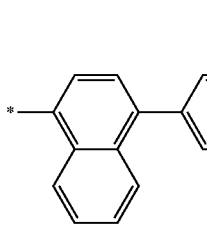
Formula 6-8
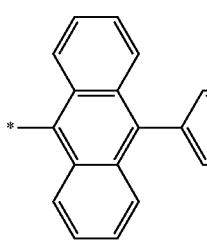
Formula 6-9
Formula 6-10
Formula 6-11
Formula 6-12
Formula 6-13
Formula 6-14

Formula 6-15
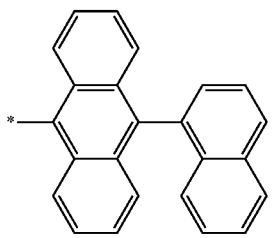

Formula 6-16
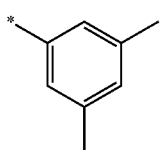

Formula 6-17
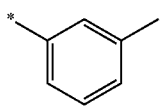

Formula 6-18
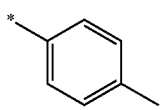

* in Formulae 6-1 to 6-18 indicates a binding site to a neighboring atom.

In Formula 1, b1 indicates the number of $R_1$, b2 indicates the number of $R_2$, b3 indicates the number of $R_3$, b4 indicates the number of $R_4$, and b5 indicates the number of $R_5$, and b1 to b5 may each independently be an integer selected from 1, 2, and 3. When b1, b2, b3, b4, or b5 is 2 or more, a plurality of $R_1$ may be identical or different, a plurality of $R_2$ may be identical or different, a plurality of $R_3$ may be identical or different, a plurality of $R_4$ may be identical or different, and/or a plurality of $R_5$ may be identical or different.

In Formula 1, c1 indicates the number of $*-[(L_1)_{n1}-(R_1)_{b1}]$, and may be an integer selected from 1, 2, 3, and 4. For example, c1 may be 1, 2, or 3. When c1 is 2 or more, a plurality of $*-[(L_1)_{n1}-(R_1)_{b1}]$ may be identical or different.

In an implementation, in Formula 1, $R_6$ and $R_7$ may each independently be selected from a substituted or unsubstituted $C_6$-$C_{20}$ aryl group and a substituted or unsubstituted monovalent non-aromatic condensed polycyclic group, and $R_6$ and $R_7$ may be linked to each other via a single bond or a substituted or unsubstituted $C_1$-$C_5$ alkylene group.

In an implementation, $R_6$ and $R_7$ in Formula 1 may each independently be selected from:
a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, and a chrysenyl group; and
a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, and a chrysenyl group.

In an implementation, $R_6$ and $R_7$ may be linked to each other via a single bond. For example, their linking structure may be exemplarily illustrated in Formula 1A.

In an implementation, the condensed cyclic compound represented by Formula 1 may be represented by Formula 1A below.

<Formula 1A>
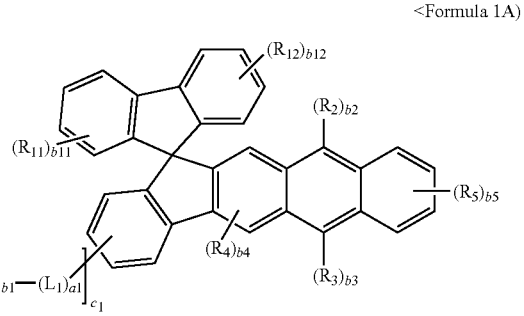

In Formula 1A, $L_1$, a1, $R_1$ to $R_7$, b1 to b5 and c1 may be the same as have already been explained above with respect to Formula 1, $R_{11}$ and $R_{12}$ may each independently be the same as explained in connection with $R_1$, and b11 and b12 are each independently selected from 0, 1, 2, 3, and 4.

In an implementation, the condensed cyclic compound may be represented by one of Formulae 1(1) to 1(6) below.

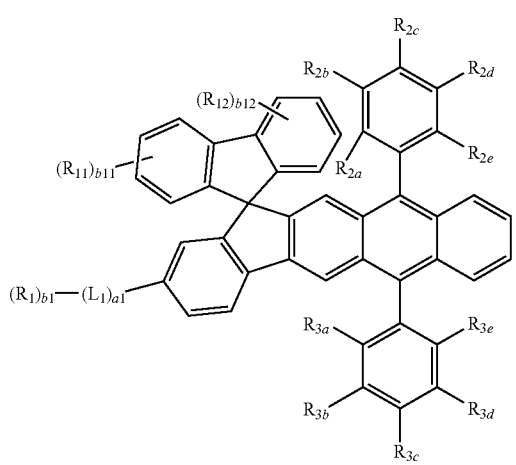

<Formula 1(2)>
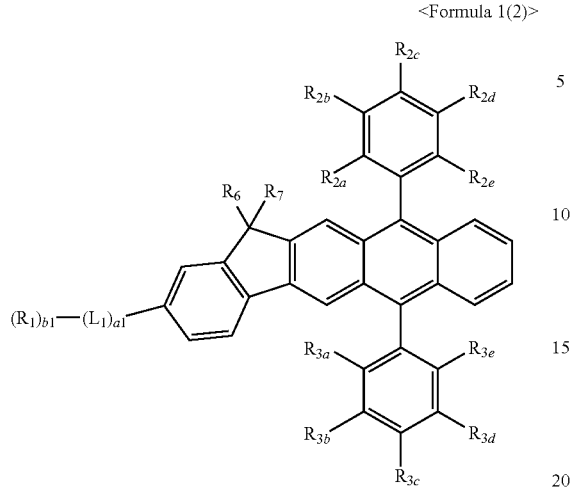
<Formula 1(3)>
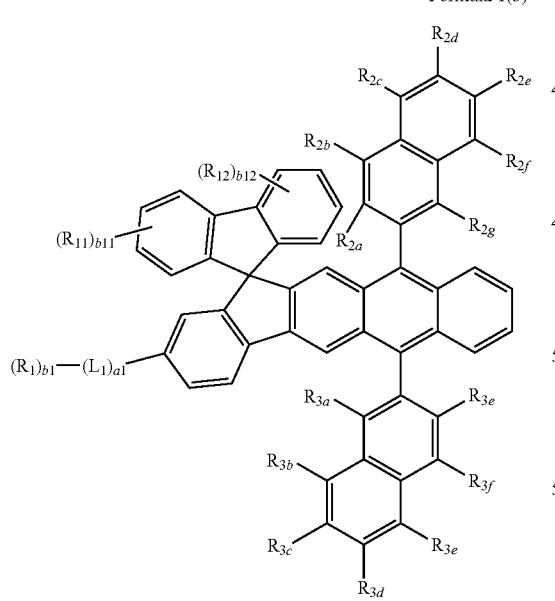
<Formula 1(4)>
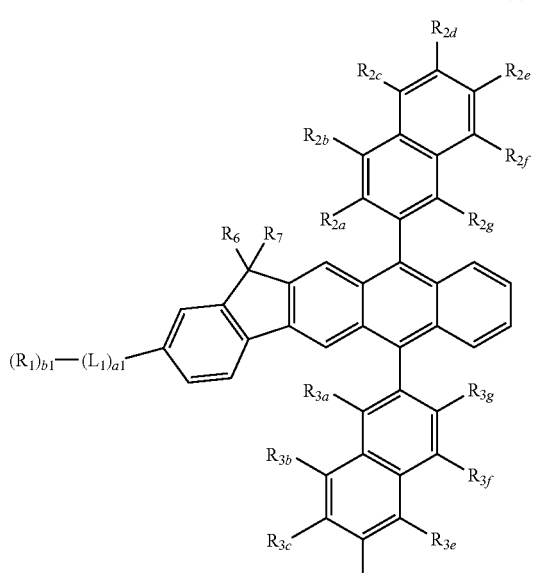
<Formula 1(5)>
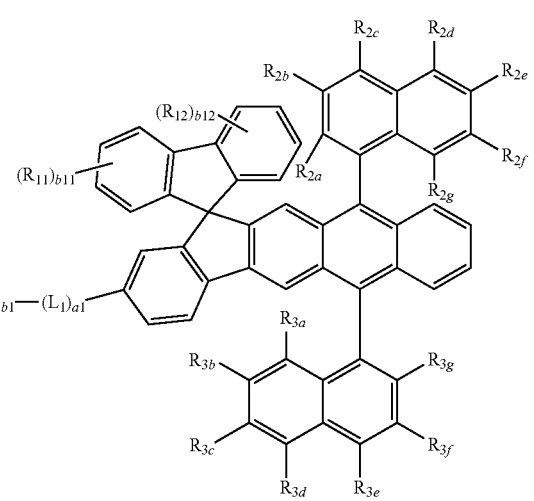
<Formula 1(6)>
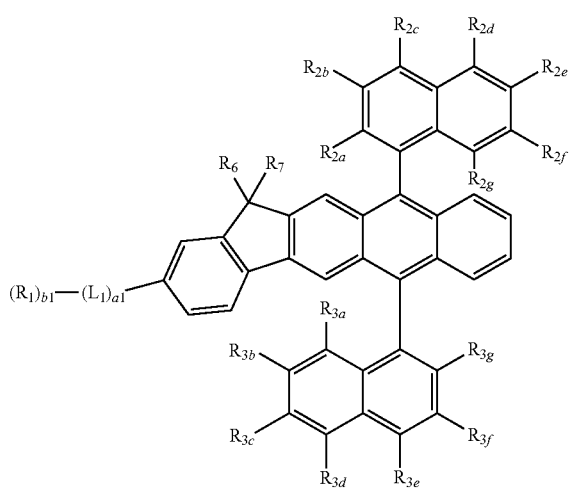
In Formulae 1(1) to 1(6), $L_1$, a1, $R_1$, $R_6$, $R_7$, and b1 may be the same as have already been explained with respect to Formula 1, $R_{11}$ and $R_{12}$ are each independently the same as explained in connection with $R_1$ of Formula 1, $R_{2a}$ to $R_{2g}$ are each independently the same as explained in connection with $R_2$ of Formula 1, $R_{3a}$ to $R_{3g}$ are each independently the same as explained in connection with $R_3$ of Formula 1, and $b_{11}$ and $b_{12}$ may each independently be selected from 0, 1, 2, 3, and 4.

In an implementation, in Formulae 1(1) to 1(6), a1 may be equal to b1 and a1 and b1 may each be 1, e.g., both a1 and b1 may be 1.

In an implementation, $L_1$ in Formulae 1(1) to 1(6) may each independently be selected from a group represented by one of Formulae 4-1 to 4-15 below.

In an implementation, $R_1$, $R_6$, and $R_7$ in Formulae 1(1) to 1(6) may each independently be selected from a $C_1$-$C_{20}$ alkyl group, a $C_1$-$C_{20}$ alkoxy group, and a group represented by one of Formulae 6-1 to 6-18.

In an implementation, the condensed cyclic compound represented by Formula 1 may be one of Compounds 1 to 15 below.

1

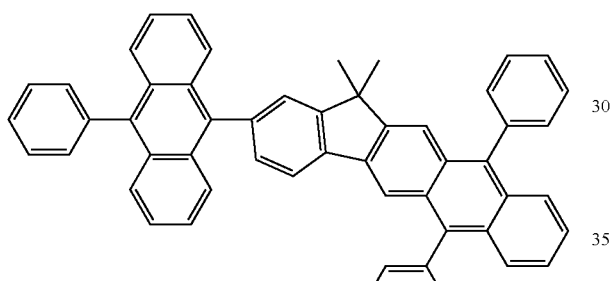

2

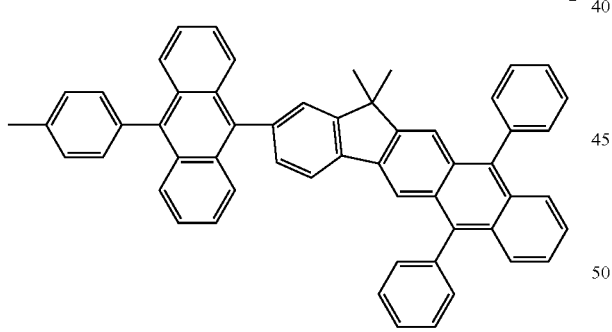

3

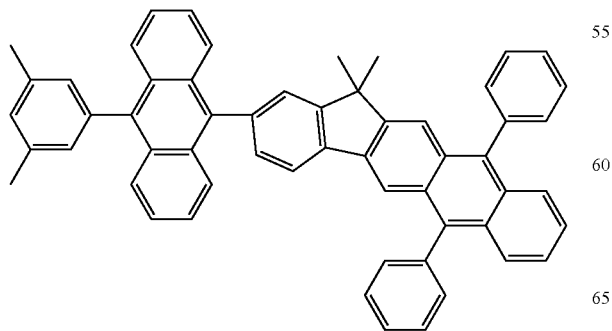

-continued

4

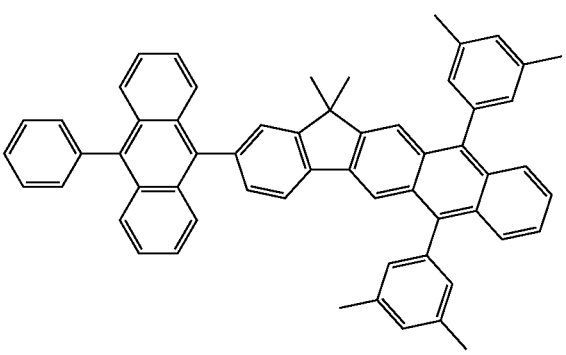

5

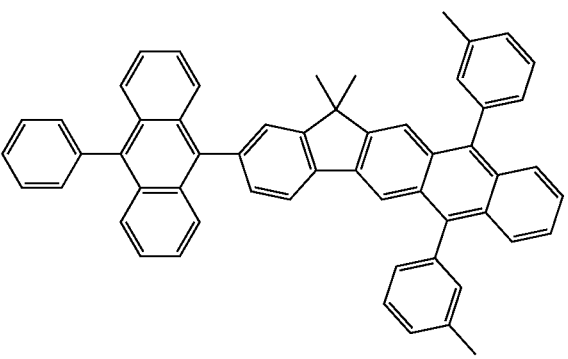

6

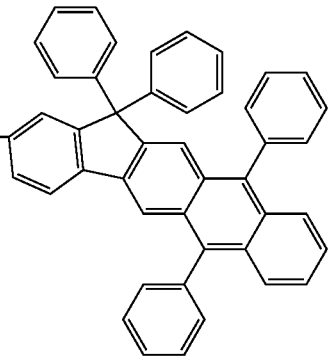

7

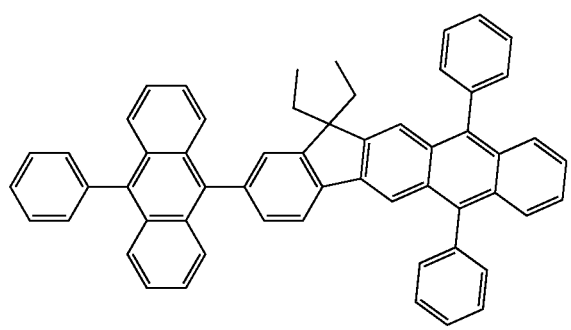

8

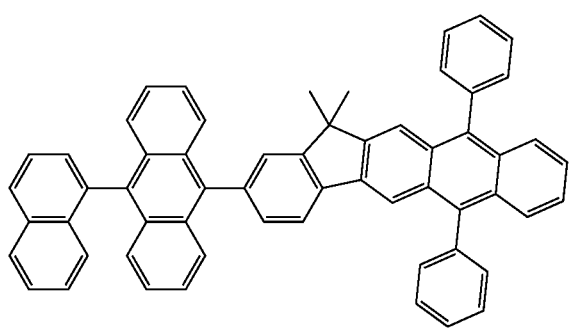

9

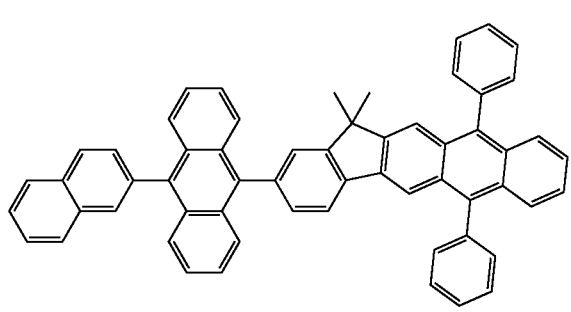

10

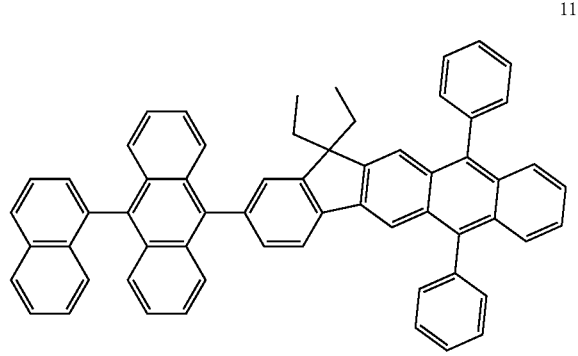

11

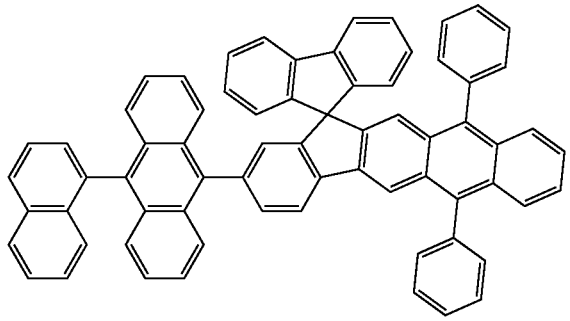

12

13

14

15

The condensed cyclic compound represented by Formula 1 may include a core moiety represented by Formula 1' below. The core moiety represented by Formula 1' may have a substantially planar structure in terms of a stereostructure, holes and electrons easily move, and a conjugation length appropriate for a blue emission material may be obtained. Accordingly, an organic light-emitting device including a compound having the core moiety may have high efficiency.

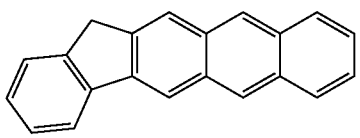

<Formula 1'>

The core moiety represented by Formula 1' in the condensed cyclic compound represented by Formula 1 may not be substituted with a heterocyclic group. If a condensed cyclic compound were to be substituted with a heterocyclic group, the heterocyclic group could cause election withdrawing and thus, a band gap could be relatively narrowed and redshift could occur. Such a condensed cyclic compound may not be appropriate for use as a material for an organic light-emitting device, e.g., a blue emission material.

The condensed cyclic compound represented by Formula 1 may be synthesized by using a suitable organic synthetic method. A synthesis method of the condensed cyclic compound may be understood in view of the following embodiments.

At least one of the condensed cyclic compound of Formula 1 may be used or included between a pair of electrodes of an organic light-emitting device. In an implementation, the condensed cyclic compound may be included an electron transport region, e.g., an electron transport layer. Accordingly, an organic light-emitting device according to an embodiment may include, e.g., a first electrode; a second electrode facing the first electrode; and an organic layer that is disposed between the first electrode and the second electrode and includes an emission layer. The organic layer includes at least one of the condensed cyclic compounds described above.

The expression that "(an organic layer) includes at least one condensed cyclic compound" used herein may include a case in which "(an organic layer) includes identical compounds represented by Formula 1 and a case in which (an organic layer) includes 2 or more different condensed cyclic compounds represented by Formula 1.

For example, the organic layer may include, as the condensed cyclic compound, only Compound 1. In this regard, Compound 1 may exist in an emission layer of the organic light-emitting device. In another embodiment, the organic layer may include, as the condensed cyclic compound, Compound 1 and Compound 2. In this regard, Compound 1 and Compound 2 may exist in an identical layer (for example, Compound 1 and Compound 2 may all exist in an emission layer), or different layers (for example, Compound 1 may exist in an emission layer and Compound 2 may exist in an electron transport layer).

The organic layer may include i) a hole transport region that is disposed between the first electrode (anode) and the emission layer and includes at least one of a hole injection layer, a hole transport layer, a buffer layer, and an electron blocking layer, and ii) an electron transport region that is disposed between the emission layer and the second electrode (cathode) and includes at least one selected from a hole blocking layer, an electron transport layer, and an electron injection layer. The emission layer may include the condensed cyclic compound represented by Formula 1.

The term "organic layer" used herein refers to a single layer and/or a plurality of layers disposed between the first electrode and the second electrode of an organic light-emitting device. A material included in the "organic layer" is not limited to an organic material.

FIG. 1 illustrates a schematic view of an organic light-emitting device 10 according to an embodiment. The organic light-emitting device 10 may include a first electrode 110, an organic layer 150, and a second electrode 190.

Hereinafter, the structure of an organic light-emitting device according to an embodiment, and a method of manufacturing an organic light-emitting device according to an embodiment, will be described in connection with FIG. 1.

In FIG. 1, a substrate may be additionally disposed under the first electrode 110 or above the second electrode 190. The substrate may be a glass substrate or transparent plastic substrate, each with excellent mechanical strength, thermal stability, transparency, surface smoothness, ease of handling, and water repellency.

The first electrode 110 may be formed by depositing or sputtering a material for forming the first electrode on the substrate. When the first electrode 10 is an anode, the material for the first electrode may be selected from materials with a high work function to make holes be easily injected. The first electrode 110 may be a reflective electrode or a transmissive electrode. The material for the first electrode may be a transparent and highly conductive material, and examples of such a material are indium tin oxide (ITO), indium zinc oxide (IZO), tin oxide ($SnO_2$), and zinc oxide (ZnO). When the first electrode 110 is a semi-transmissive electrode or a reflective electrode, as a material for forming the first electrode, at least one of magnesium (Mg), aluminum (Al), aluminum-lithium (Al—Li), calcium (Ca), magnesium-indium (Mg—In), magnesium-silver (Mg—Ag) may be used.

The first electrode 110 may have a single-layer structure, or a multi-layer structure including 2 or more layers. For example, the first electrode 110 may have a three-layered structure of ITO/Ag/ITO.

The organic layer 150 is disposed on the first electrode 110. The organic layer 150 may include an emission layer.

The organic layer 150 may further include a hole transport region disposed between the first electrode and the emission layer, and an electron transport region disposed between the emission layer and the second electrode.

The hole transport region may include at least one selected from a hole injection layer (HIL), a hole transport layer (HTL), a buffer layer, and an electron blocking layer (EBL), and the electron transport region may include at least one selected from a hole blocking layer (HBL), an electron transport layer (ETL), and an electron injection layer (EIL).

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, or a structure of hole injection layer/hole transport layer, a structure of hole injection layer/hole transport layer/buffer layer, a structure of hole injection layer/buffer layer, a structure of hole transport layer/buffer layer, or a structure of hole injection layer/hole transport layer/electron blocking layer, wherein layers of each structure are sequentially stacked from the first electrode 110 in this stated order.

When the hole transport region includes a hole injection layer, the hole injection layer may be formed on the first electrode 110 by using various methods, such as vacuum deposition, spin coating casting, a Langmuir-Blodgett (LB) method, ink-jet printing, laser-printing, or laser-induced thermal imaging.

When a hole injection layer is formed by vacuum deposition, e.g., the vacuum deposition may be performed at a temperature of a deposition temperature of about 100 to about 500° C., at a vacuum degree of about $10^{-8}$ to about $10^{-3}$ torr, and at a deposition rate of about 0.01 to about 100 Å/sec in consideration of a compound for a hole injection layer to be deposited, and the structure of a hole injection layer to be formed.

When a hole injection layer is formed by spin coating, the spin coating may be performed at a coating rate of about 2,000 rpm to about 5,000 rpm, and at a temperature of about 80° C. to 200° C. in consideration of a compound for a hole injection layer to be deposited, and the structure of a hole injection layer to be formed.

When the hole transport region includes a hole transport layer, the hole transport layer may be formed on the first electrode 110 or the hole injection layer by using various methods, such as vacuum deposition, spin coating, casting, a LB method, ink-jet printing, laser-printing, or laser-induced thermal imaging. When the hole transport layer is formed by vacuum deposition or spin coating, deposition and coating conditions for the hole transport layer may be determined by referring to the deposition and coating conditions for the hole injection layer.

The hole transport region may include at least one selected from m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (PANI/CSA), (polyaniline)/poly(4-styrenesulfonate) (Pani/PSS), a compound represented by Formula 201 below, and a compound represented by Formula 202 below.

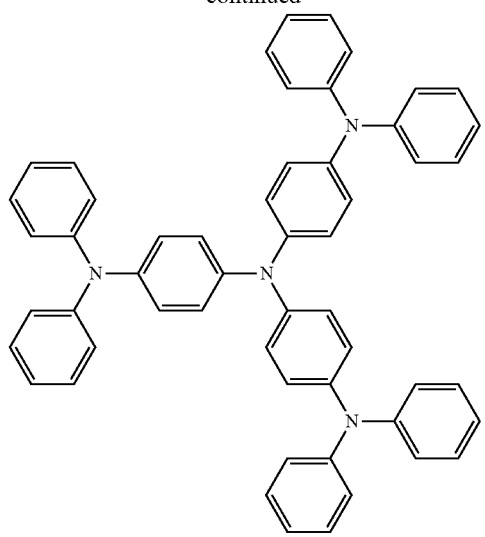

TDATA

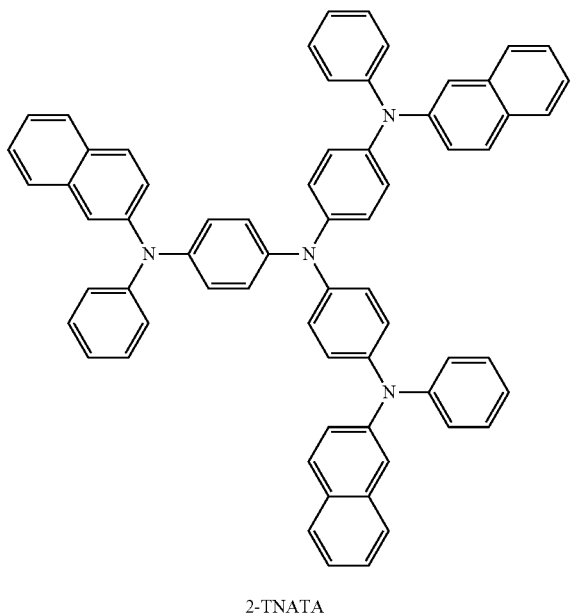

2-TNATA

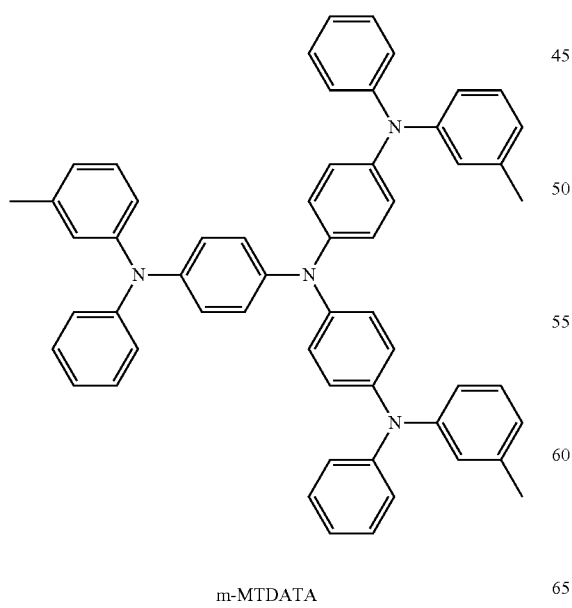

m-MTDATA

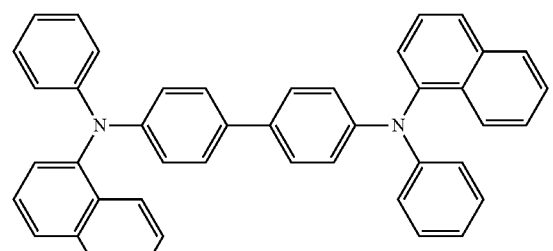

NPB

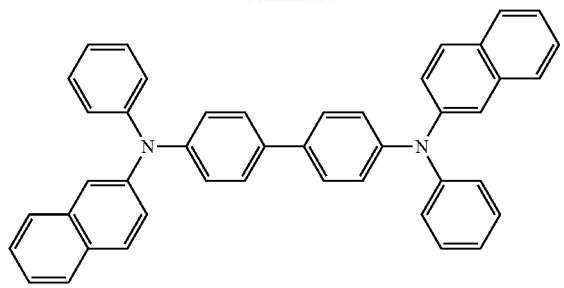

β–NPB

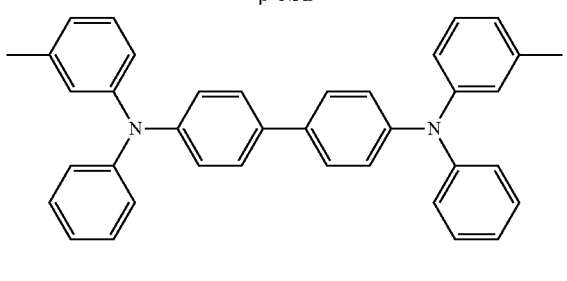

TPD

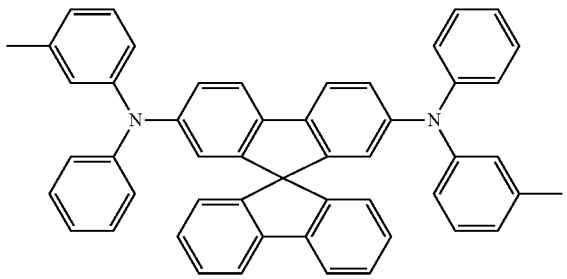

Spiro-TPD

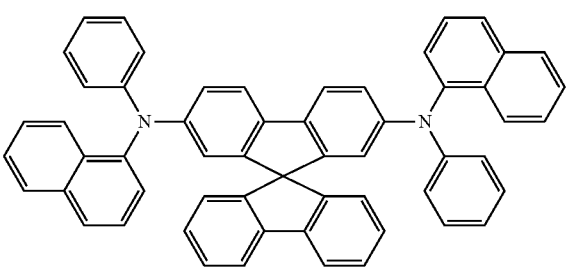

Spiro-NPB

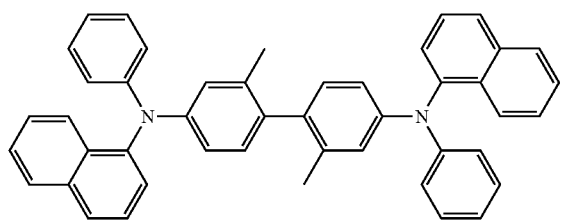

methylated NPB

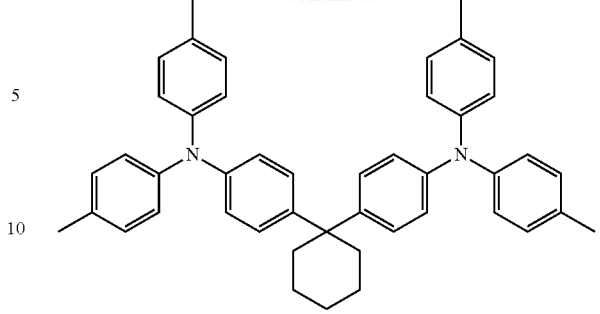

TAPC

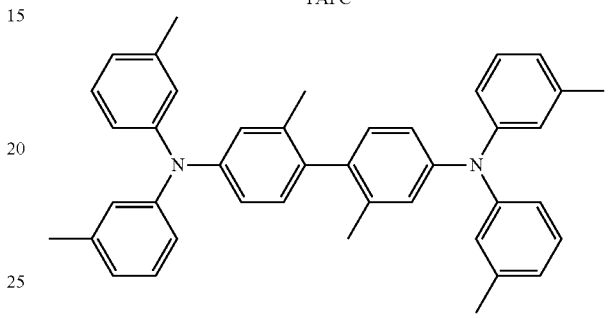

HMTPD

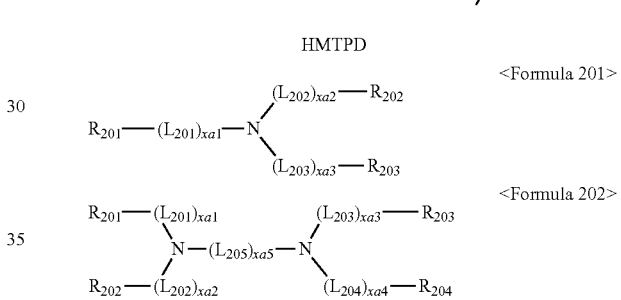

<Formula 201>

<Formula 202>

In Formulae 201 and 202, $L_{201}$ to $L_{205}$ may be the same as explained in connection with $L_1$ to $L_3$;

xa1 to xa4 may each independently be selected from 0, 1, 2, and 3;

xa5 may be selected from 1, 2, 3, 4, and 5; and $R_{201}$ to $R_{204}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In Formulae 201 and 202, $L_{201}$ to $L_{205}$ may each independently be selected from a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may each independently be 0, 1, or 2;

xa5 may be 1, 2, or 3;

$R_{201}$ to $R_{204}$ may each independently be selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

The compound represented by Formula 201 may be represented by Formula 201A.

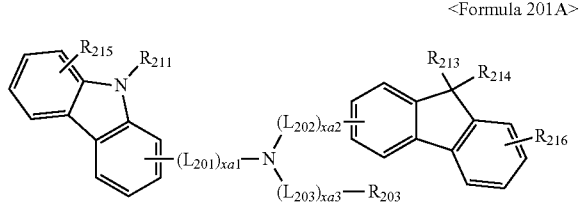

<Formula 201A>

For example, the compound represented by Formula 201 may be represented by Formula 201A-1 below.

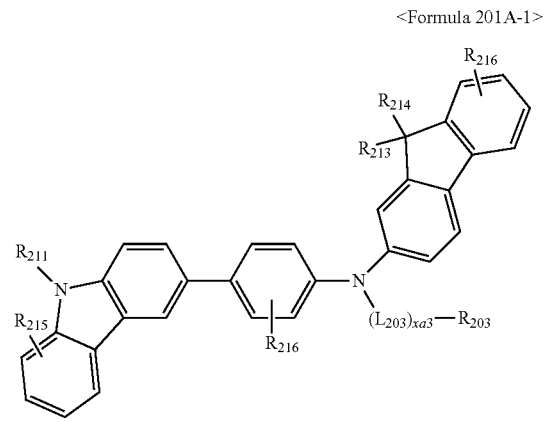

<Formula 201A-1>

For example, the compound represented by Formula 202 may be represented by Formula 202A below.

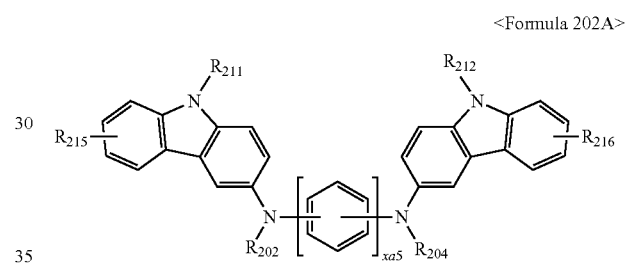

<Formula 202A>

$L_{201}$ to $L_{203}$, xa1 to xa3, xa5, and $R_{202}$ to $R_{204}$ in Formulae 201A, 201A-1, and 202A are already described above, $R_{211}$ is the same as defined in connection with $R_{203}$, and $R_{213}$ to $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

For example, in Formulae 201A, 201A-1, and 202A, $L_{201}$ to $L_{203}$ may each independently be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may each independently be 0 or 1;

$R_{203}$, $R_{211}$, and $R_{212}$ may each independently be selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ may each independently be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa5 may be 1 or 2.

$R_{213}$ and $R_{214}$ in Formulae 201A, and 201A-1 may bind to each other to form a saturated or unsaturated ring.

The compound represented by Formula 201, and the compound represented by Formula 202 may each include compounds HT1 to HT20 illustrated below.

HT1

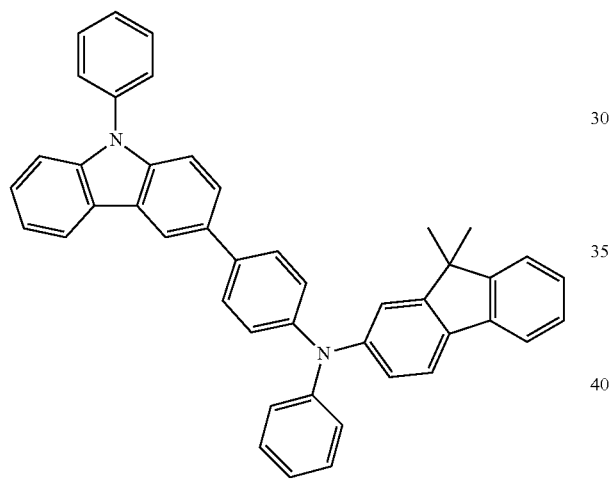

HT2

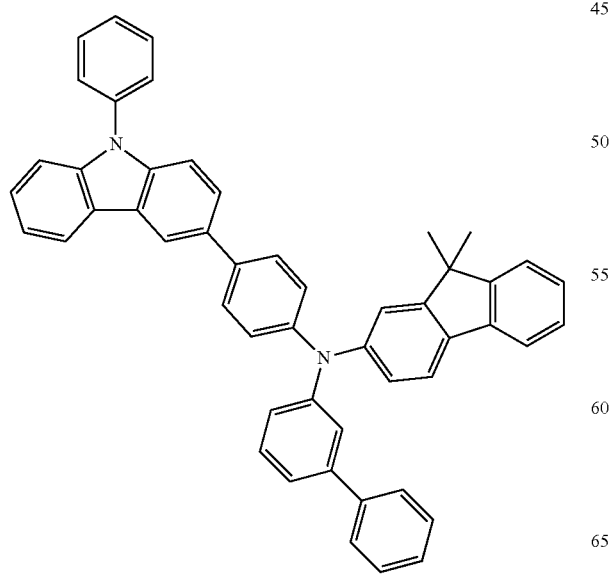

HT3

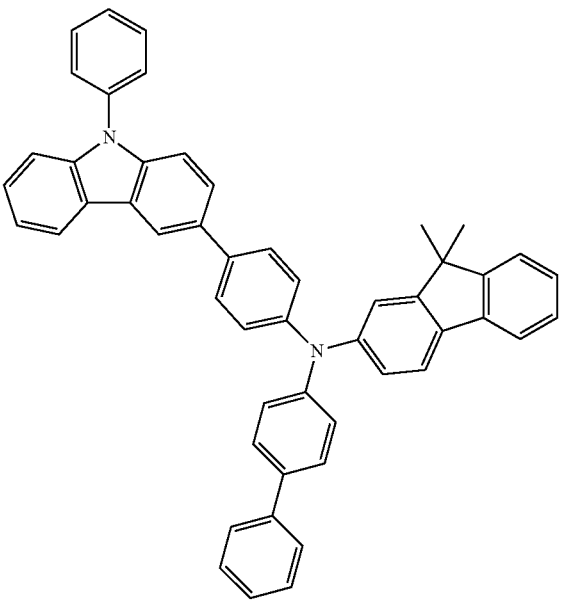

HT4

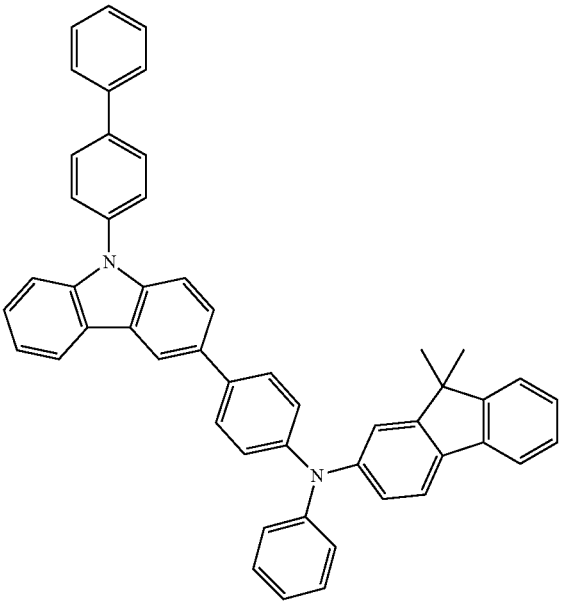

HT5
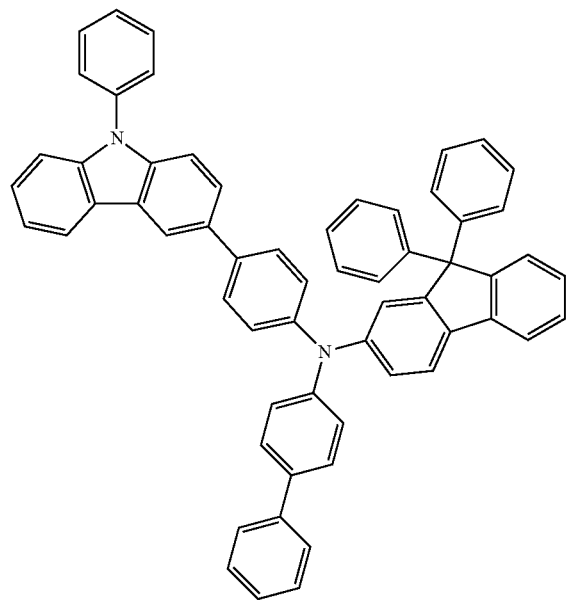
HT6
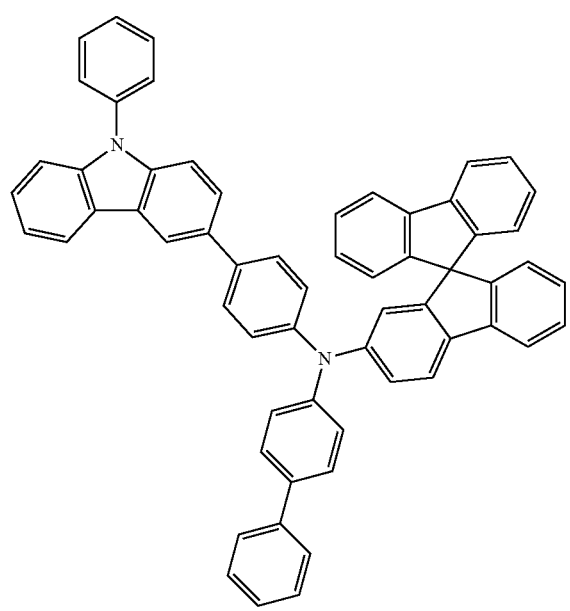
HT7
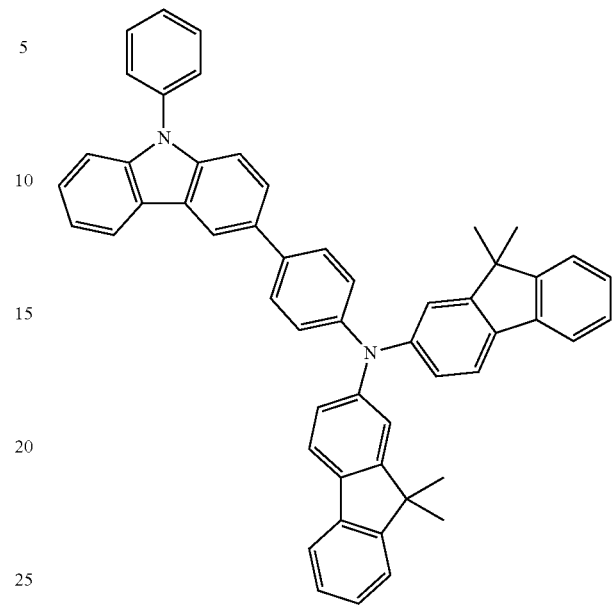
HT8

HT9
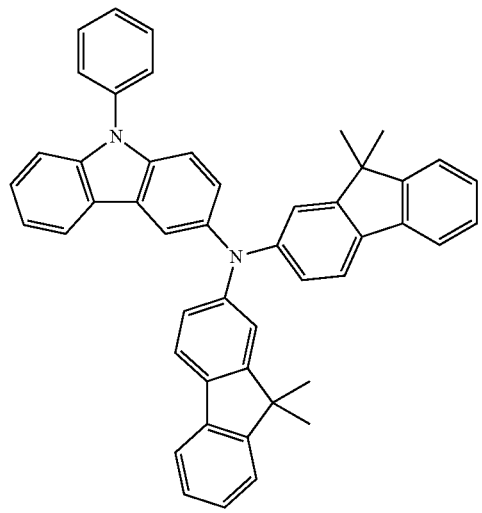
HT11
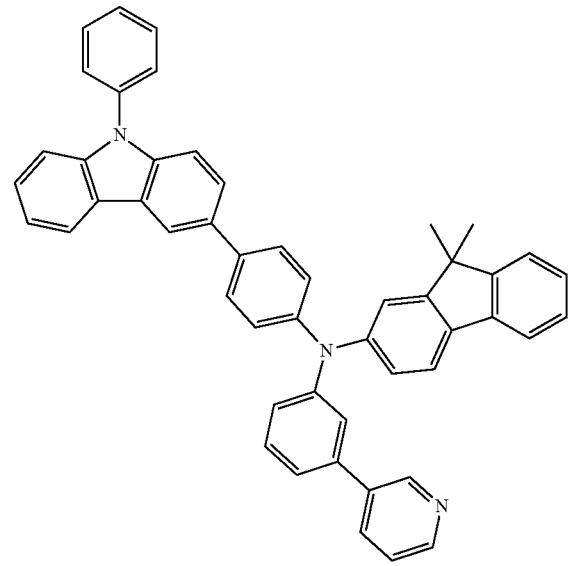
HT12
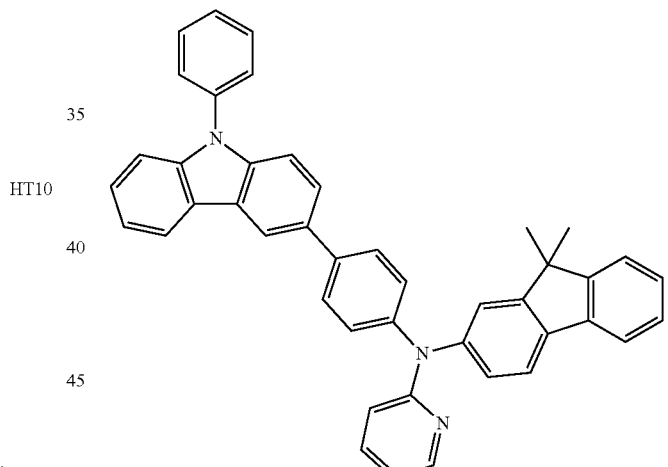
HT10
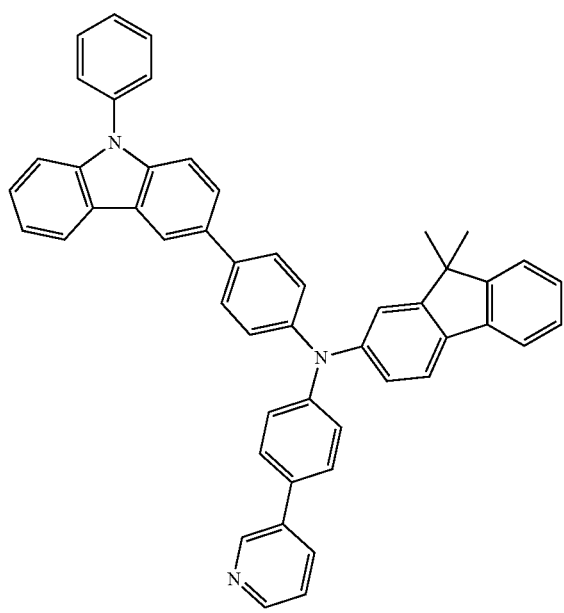
HT13
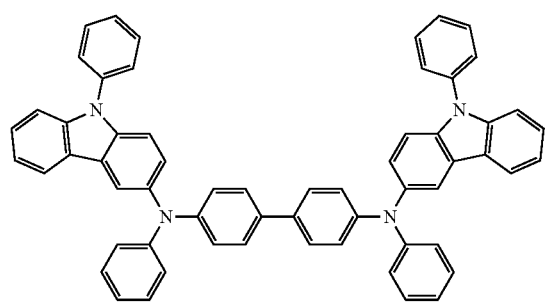

-continued

HT14
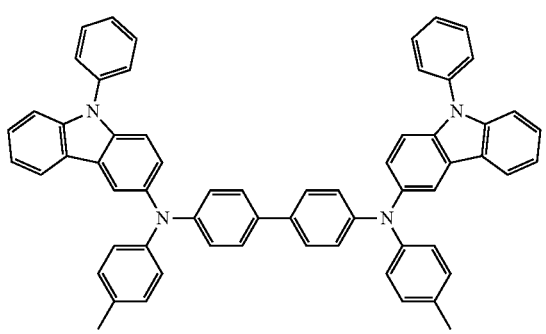

HT15
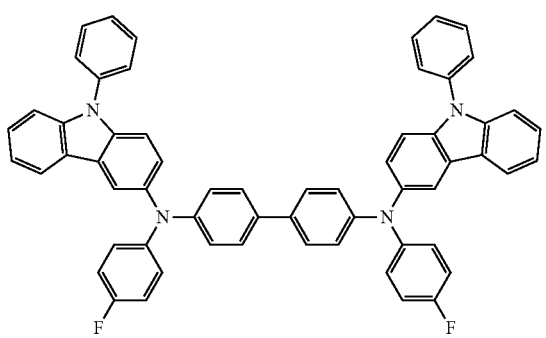

HT16
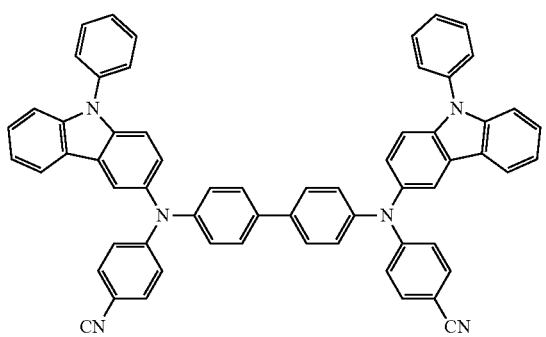

HT17
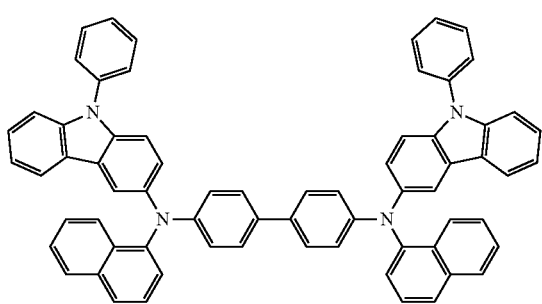

-continued

HT18
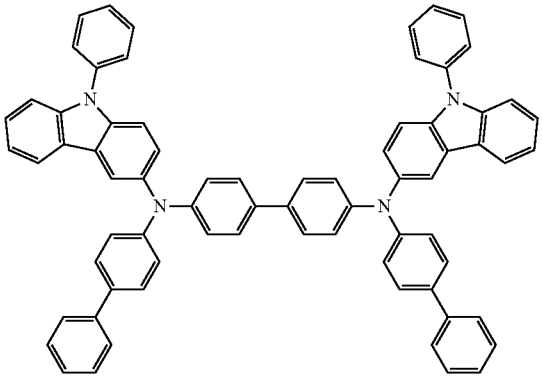

HT19
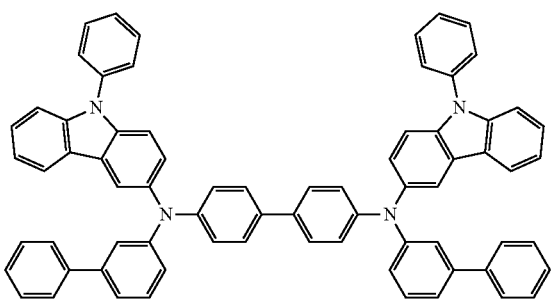

HT20
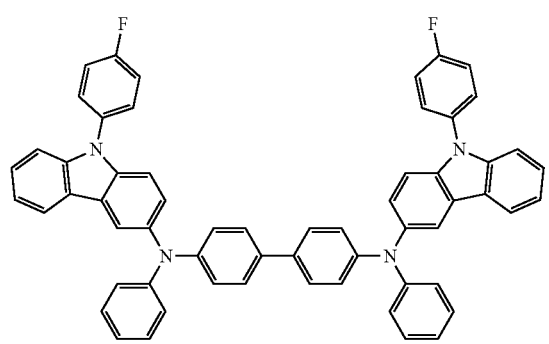

A thickness of the hole transport region may be in a range of about 100 Å to about 10,000 Å, e.g., about 100 Å to about 1,000 Å. When the hole transport region includes a hole injection layer and a hole transport layer, the thickness of the hole injection layer may be in a range of about 100 Å to about 10,000 Å, e.g., about 100 Å to about 1,000 Å, and the thickness of the hole transport layer may be in a range of about 50 Å to about 2,000 Å, e.g., about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, e.g., a p-dopant. The p-dopant may include one of a quinone derivative, a metal oxide, and a cyano group-containing compound. Examples of the p-dopant may include a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide, and Compound HT-D1 illustrated below.

<Compound HT-D1>

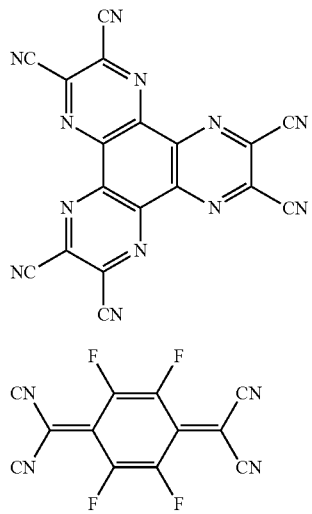

<F4-TCNQ>

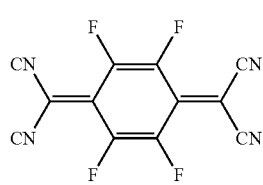

The hole transport region may further include, in addition to the hole injection layer and the hole transport layer, at least one of a buffer layer and an electron blocking layer. The buffer layer may compensate for an optical resonance distance according to a wavelength of light emitted from the emission layer, and light-emission efficiency of a formed organic light-emitting device may be improved. For use as a material included in the buffer layer, materials that are included in the hole transport region may be used. The electron blocking layer prevents injection of electrons from the electron transport region.

The emission layer may be formed on the first electrode 110 or the hole transport region by using various methods, e.g., vacuum deposition, spin coating, casting, a LB method, ink-jet printing, laser-printing, or laser-induced thermal imaging. When the emission layer is formed by vacuum deposition or spin coating, deposition and coating conditions for the emission layer may be determined by referring to the deposition and coating conditions for the hole injection layer.

When the organic light-emitting device 10 is a full color organic light-emitting device, the emission layer may be patterned into a red emission layer, a green emission layer, or a blue emission layer, according to a sub pixel. In an implementation, the emission layer may have a stacked structure of a red emission layer, a green emission layer, and a blue emission layer, or may include a red-light emission material, a green-light emission material, and a blue-light emission material, which are mixed with each other in a single layer, to emit white light.

The emission layer may include the condensed cyclic compound represented by Formula 1.

The emission layer may include a host and a dopant. The host may include the condensed cyclic compound represented by Formula 1.

The host may further include, in addition to the condensed cyclic compound represented by Formula 1, at least one of TPBi, TBADN, ADN (also referred to as "DNA"), CBP, CDBP, and TCP.

TPBi

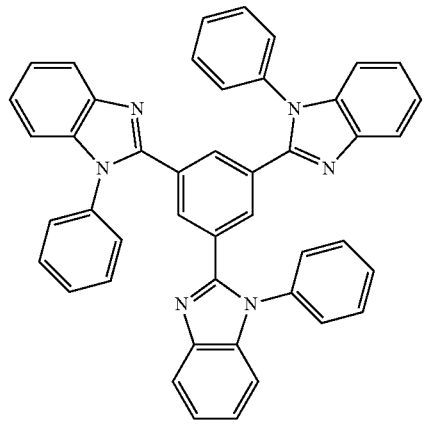

TBADN

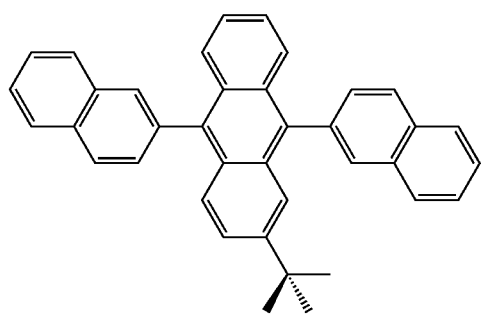

ADN

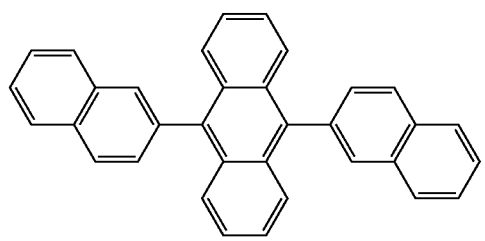

CBP

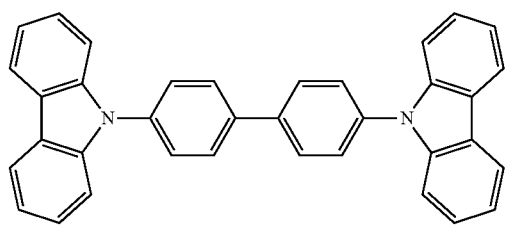

CDBP

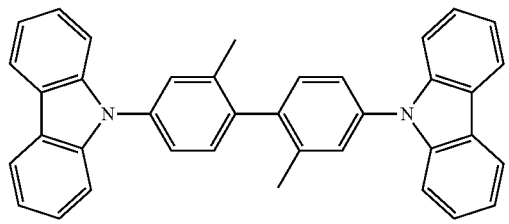

TCP

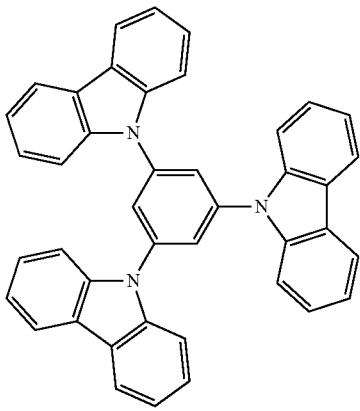

The dopant may include a fluorescent dopant and/or a phosphorescent dopant.

The phosphorescent dopant may include an organometallic complex represented by Formula 401 below.

<Formula 401>

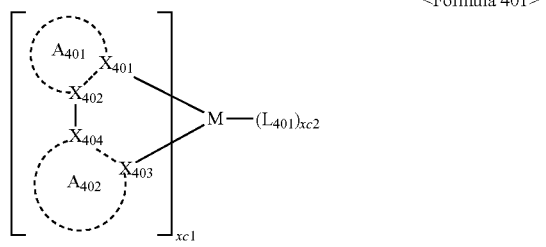

In Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may each independently be selected from nitrogen and carbon;

rings $A_{401}$ and $A_{402}$ may each independently be selected from a substituted or unsubstituted benzene, a substituted or unsubstituted naphthalene, a substituted or unsubstituted fluorenene, a substituted or unsubstituted spiro-fluorenene, a substituted or unsubstituted indene, a substituted or unsubstituted pyrrol, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazol, a substituted or unsubstituted benzoimidazole, a substituted or unsubstituted benzofuran, a substituted or unsubstituted benzothiophene, a substituted or unsubstituted isobenzothiophene, a substituted or unsubstituted benzooxazole, a substituted or unsubstituted isobenzooxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene; and at least one substituent of the substituted benzene, substituted naphthalene, substituted fluorenene, substituted spiro-fluorenene, substituted indene, substituted pyrrol, substituted thiophene, substituted furan, substituted imidazole, substituted pyrazole, substituted thiazole, substituted isothiazole, substituted oxazole, substituted isoxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazol, substituted benzoimidazole, substituted benzofuran, substituted benzothiophene, substituted isobenzothiophene, substituted benzooxazole, substituted isobenzooxazole, substituted triazole, substituted oxadiazole, substituted triazine, substituted dibenzofuran, and substituted dibenzothiophene may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), or —B($Q_{406}$)($Q_{407}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic heterocondensed polycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$); and $L_{401}$ may be an organic ligand;

xc1 may be 1, 2, or 3; and xc2 may be 0, 1, 2, or 3.

$L_{401}$ may be a monovalent, divalent, or trivalent organic ligand. For example, $L_{401}$ may be selected from a halogen ligand (for example, Cl or F), a diketone ligand (for example, acetylacetonate, 1,3-diphenyl-1,3-propandionate, 2,2,6,6-tetramethyl-3,5-heptandionate, or hexafluoroacetonate), a carboxylic acid ligand (for example, picolinate, dimethyl-3-pyrazolecarboxylate, or benzoate), a carbon monooxide ligand, an isonitrile ligand, a cyano ligand, and a phosphorous ligand (for example, phosphine, and phosphaite).

When $A_{401}$ in Formula 401 has 2 or more substituents, the substituents of $A_{401}$ may bind to each other to form a saturated or unsaturated ring.

When $A_{402}$ in Formula 401 has 2 or more substituents, the substituents of $A_{402}$ may bind to each other to form a saturated or unsaturated ring.

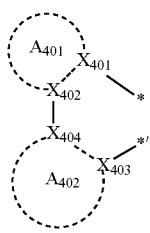

When xc1 in Formula 401 is 2 or more, a plurality of ligands in Formula 401 may be identical or different. When xc1 in Formula 401 is 2 or more, $A_{401}$ and $A_{402}$ may each be linked to $A_{401}$ and $A_{402}$ of a neighboring other ligand, directly or via a linking group (for example, a $C_1$-$C_5$ alkylene group, or —N(R')— (wherein R' is a $C_1$-$C_{10}$ alkyl group or a $C_6$-$C_{20}$ aryl group) or —C(=O)—).

The phosphorescent dopant may include at least one of Compounds PD1 to PD74 below.

PD1

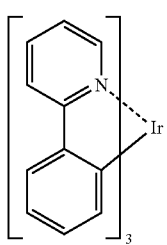

PD2

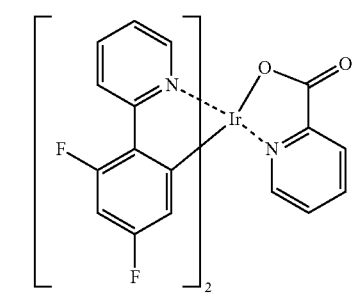

PD3

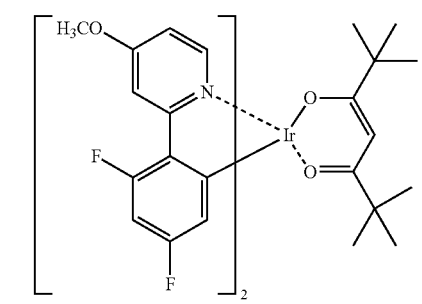

PD4

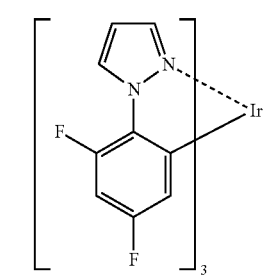

PD5

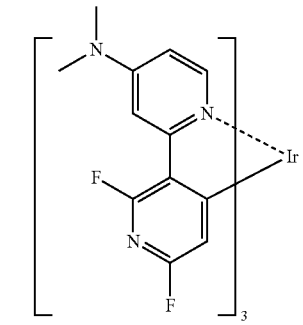

PD6

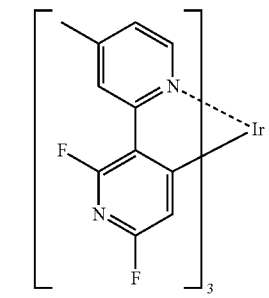

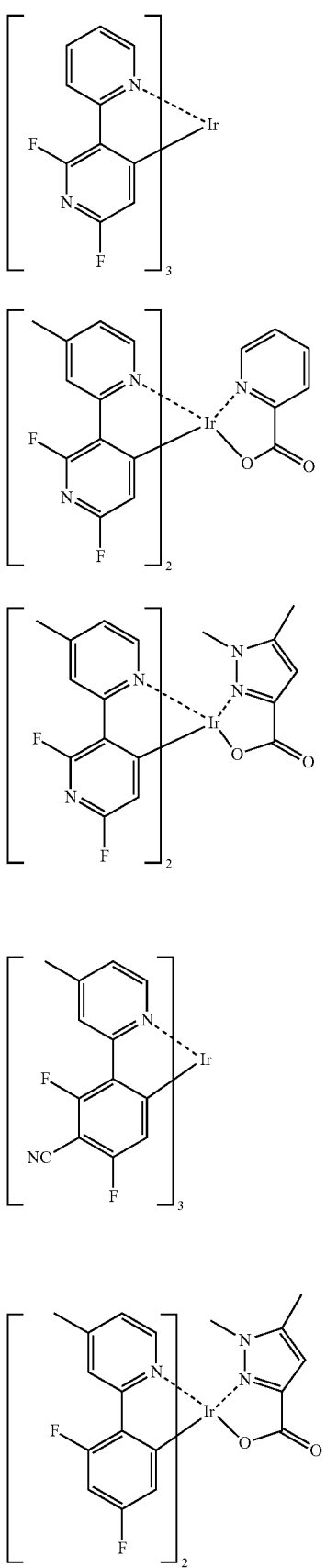
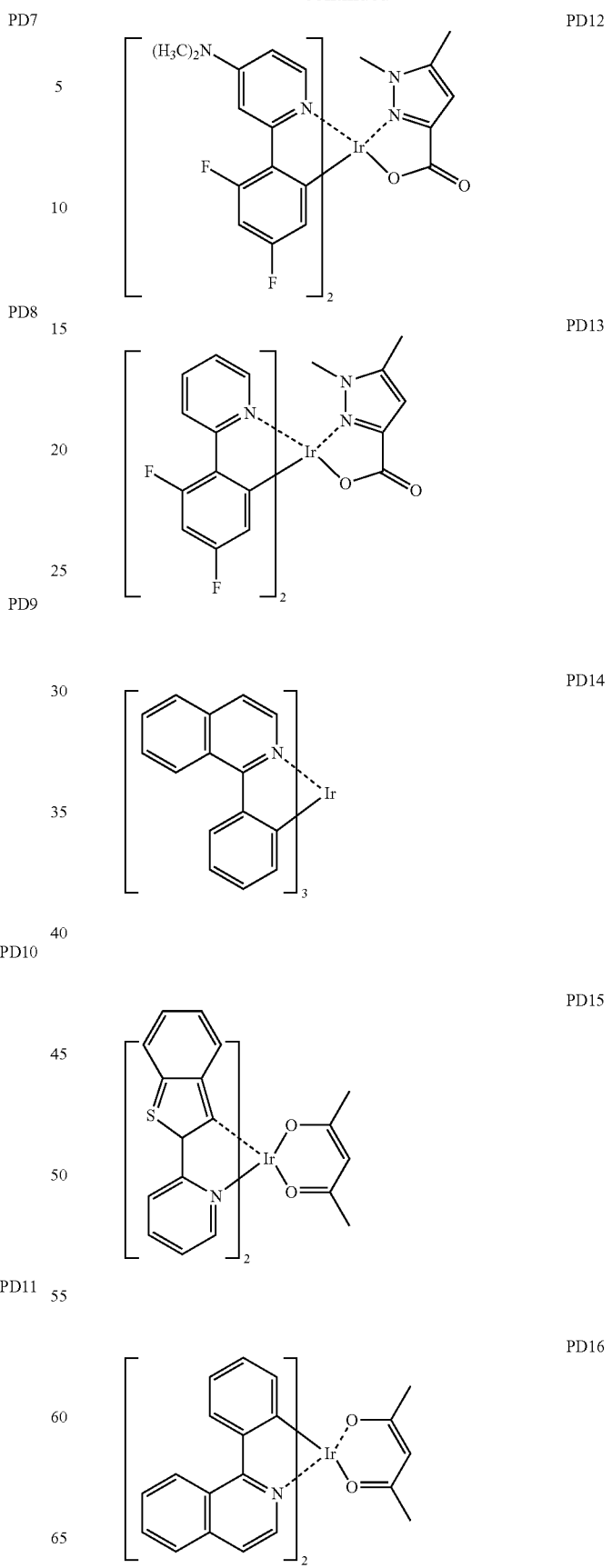

PD17
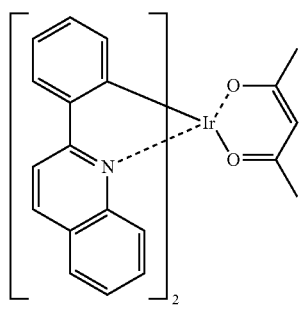
PD18
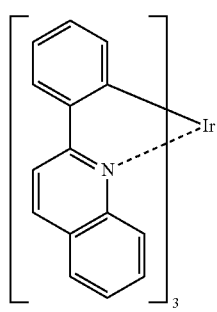
PD19
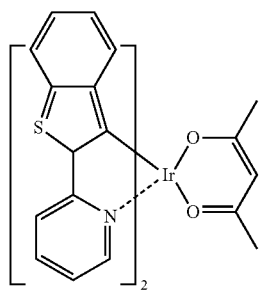
PD20
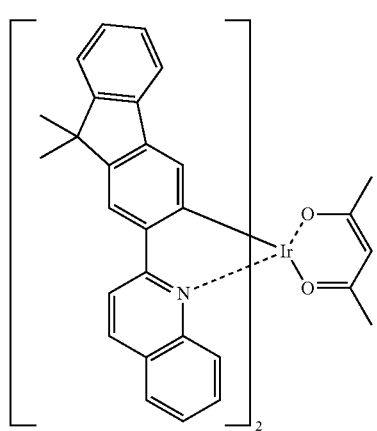
PD21
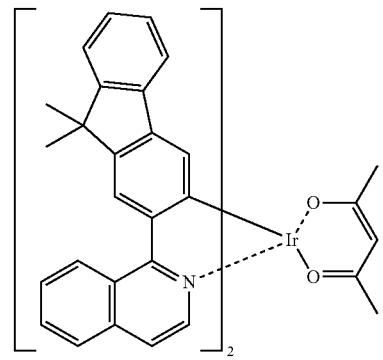
PD22
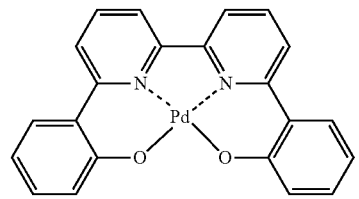
PD23
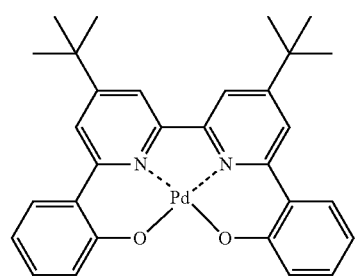
PD24
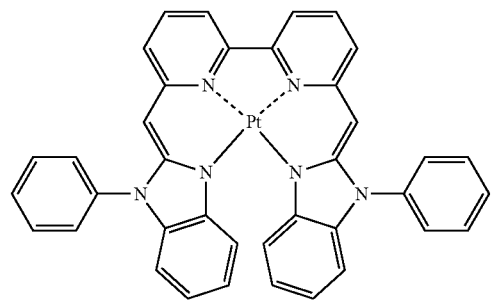
PD25
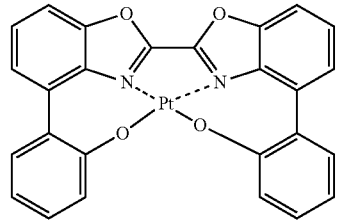
PD26

PD27 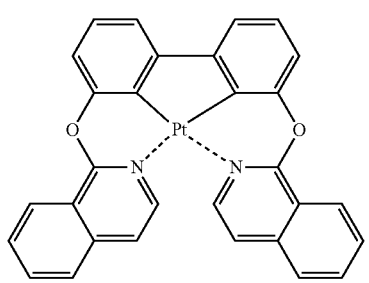
PD28 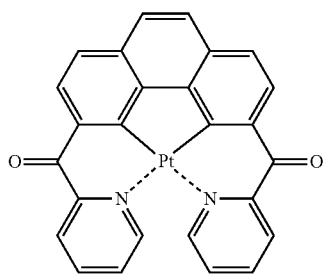
PD29 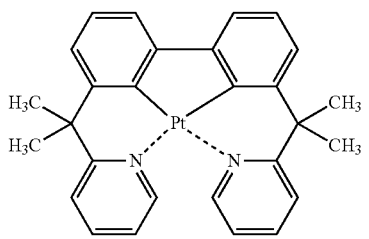
PD30 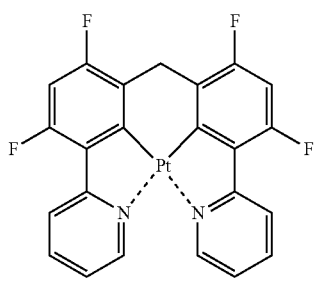
PD31 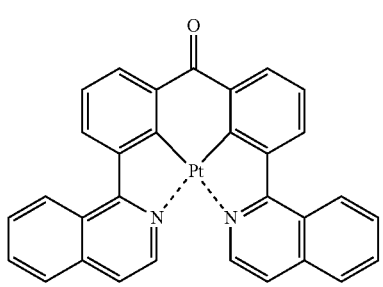
PD32 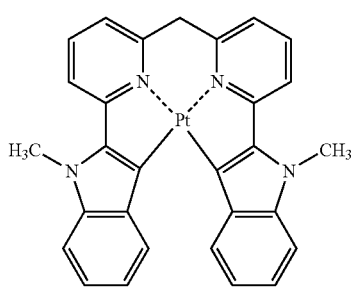
PD33 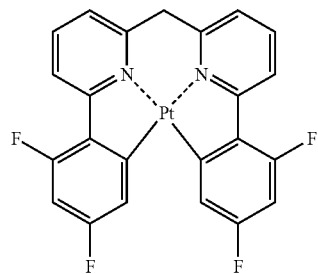
PD34 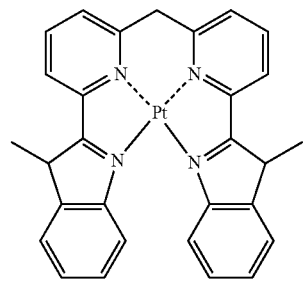
PD35 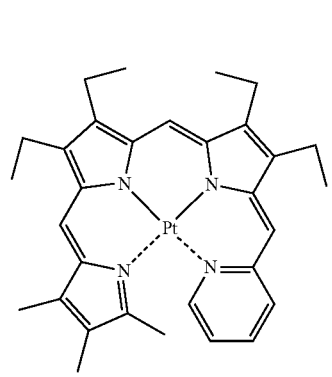
PD36 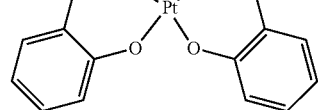
PD37 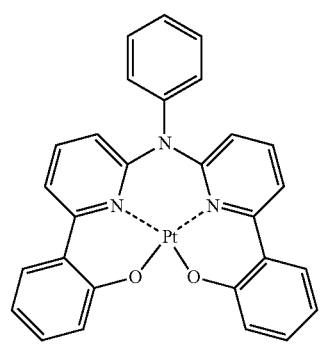

-continued
PD38
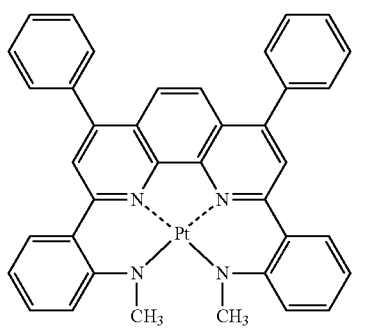
PD39
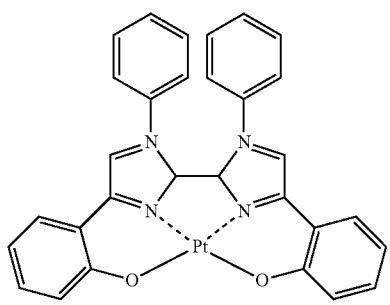
PD40
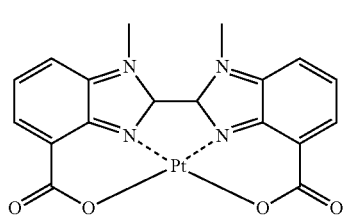
PD41
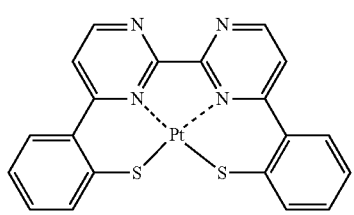
PD42
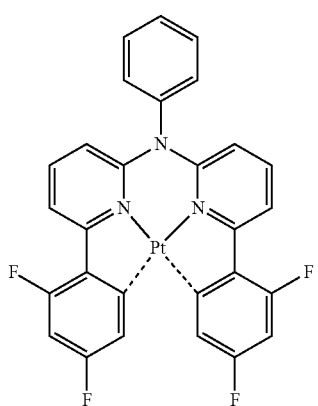
-continued
PD43
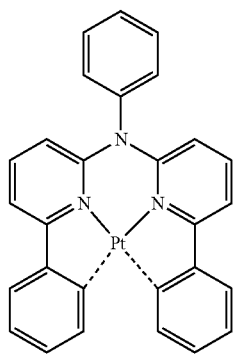
PD44
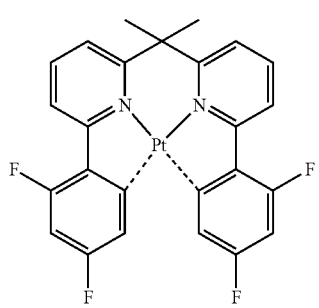
PD45
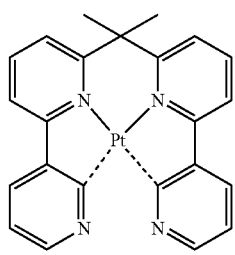
PD46
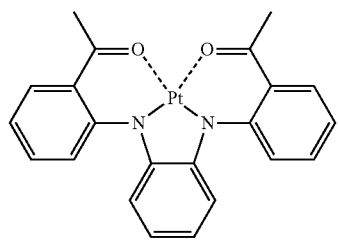
PD47
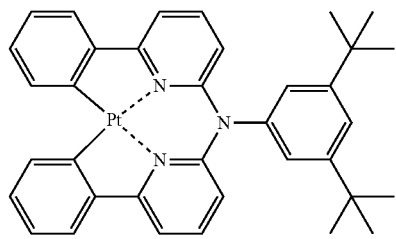
PD48
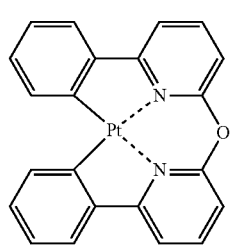

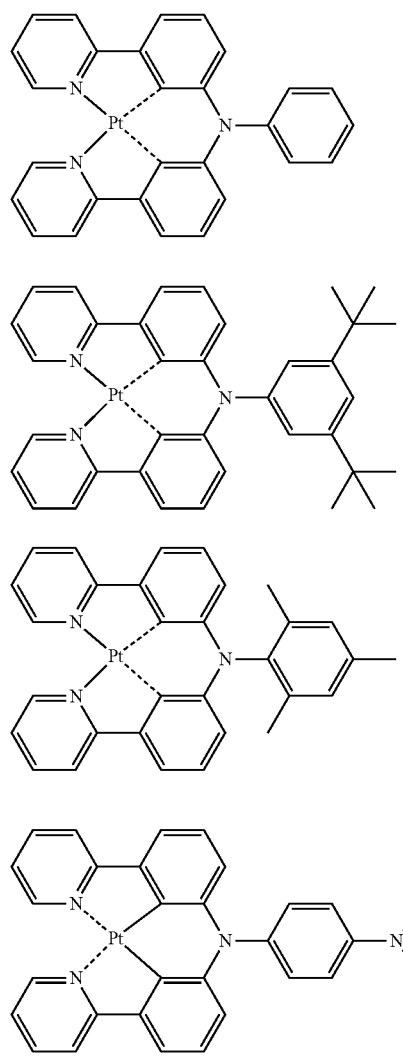
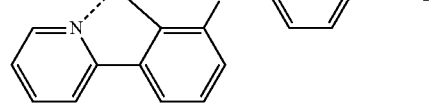
PD49
PD50
PD51
PD52
PD53
PD54
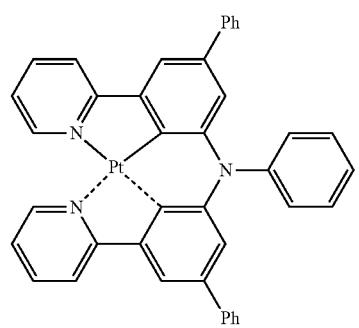
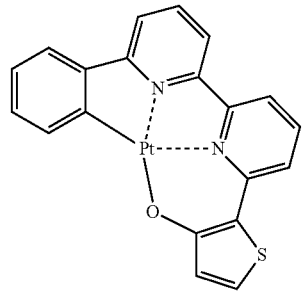
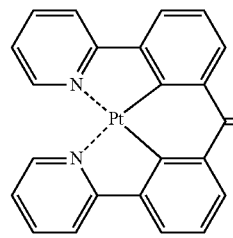
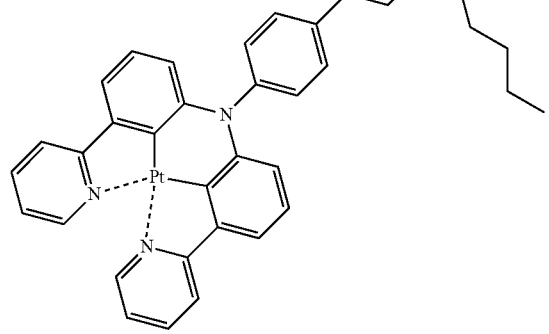
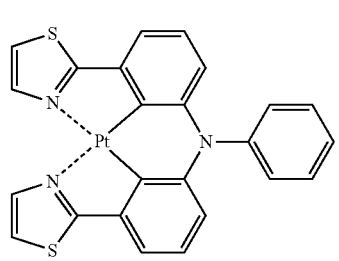
PD55
PD56
PD57
PD58
PD59

PD60 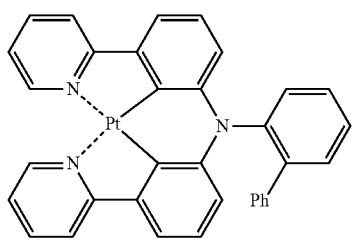
PD61 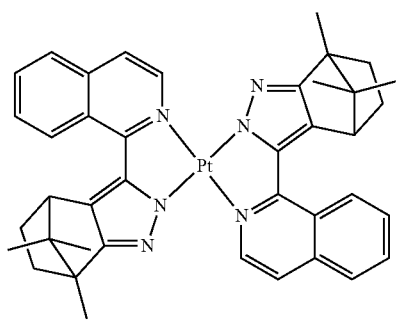
PD62 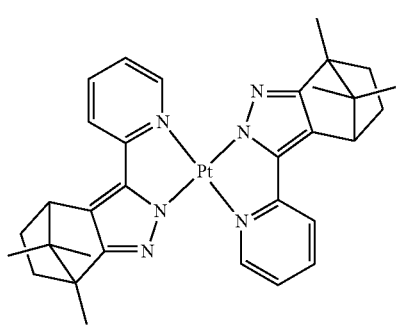
PD63 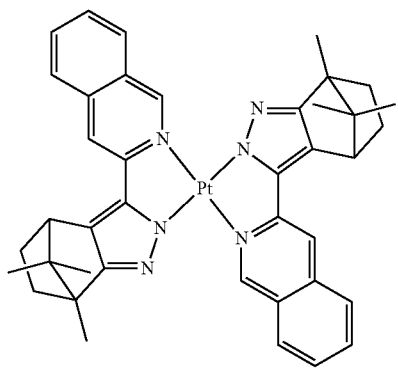
PD64 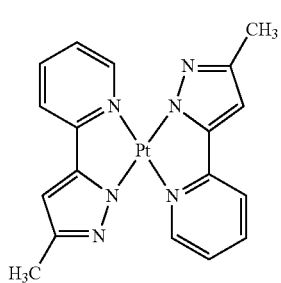
PD65 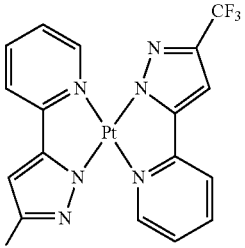
PD66 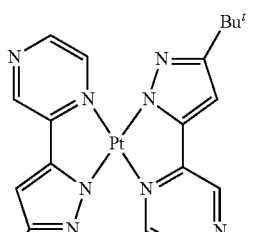
PD67 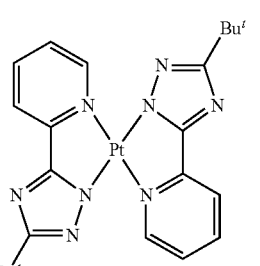
PD68 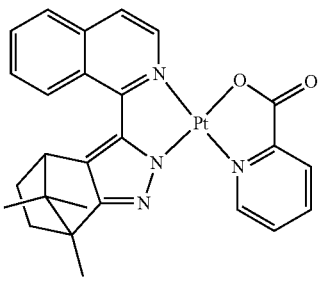
PD69 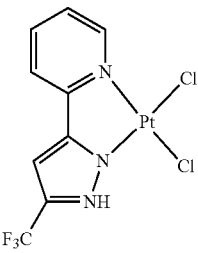

-continued
PD70 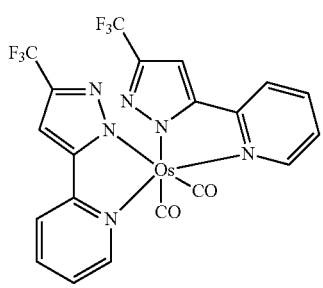
PD71 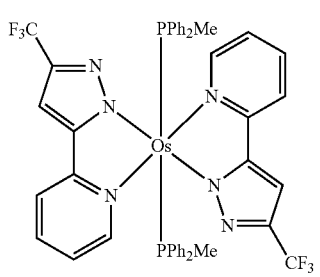
PD72 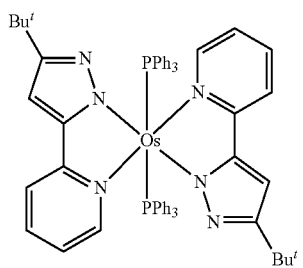
PD73 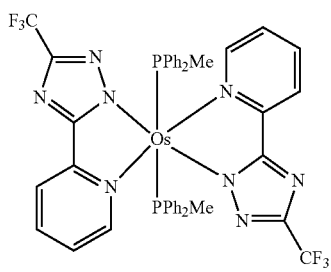
-continued
PD74 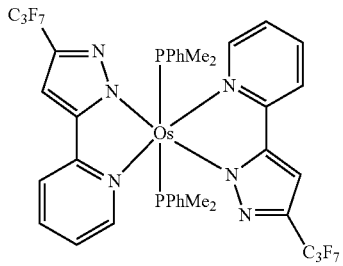
In an implementation, the phosphorescent dopant may include PtOEP.
PtOEP 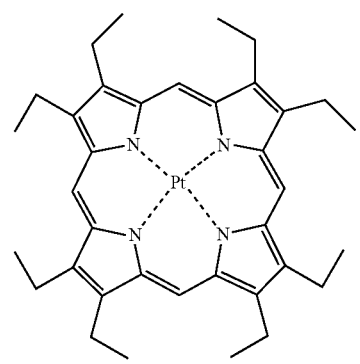
In an implementation, the fluorescent dopant may include at least one selected from DPAVBi, BDAVBi, TBPe, DCM, DCJTB, Coumarin 6, and C545T.
DPVBi
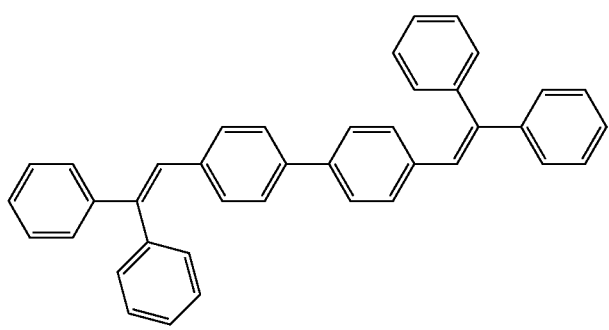

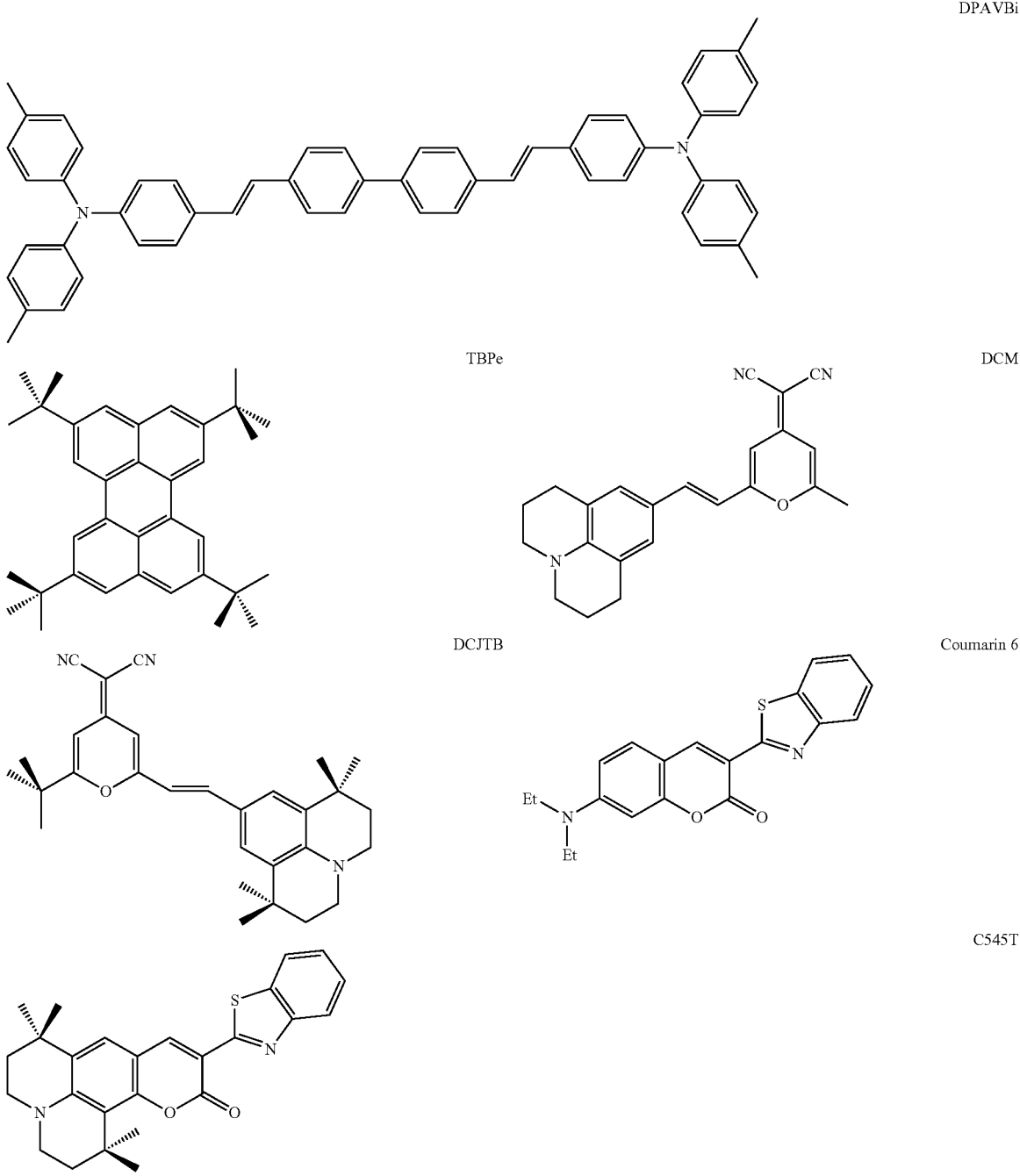

In an implementation, the fluorescent dopant may include a compound represented by Formula 501 below.

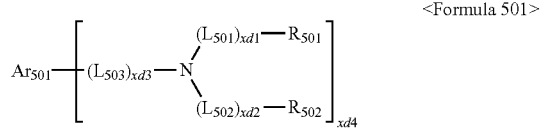

In Formula 501,
Ar$_{501}$ may be selected from
a naphthalene, a heptalene, a fluorenene, a spiro-fluorenene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene; and a naphthalene group, a heptalene group, a fluorenene group, a spiro-fluorenene group, a benzofluorenene group, a dibenzofluorenene group, a phenalene group, a phenanthrene group, a anthracene group, a fluoranthene group, a triphenylene group, a pyrene group, a chrysene group, a naphthacene group, a picene group, a perylene group, a pentaphene group, and an indenoanthracene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or —Si($Q_{501}$)($Q_{502}$)($Q_{503}$) (wherein $Q_{501}$ to $Q_{503}$ are each independently selected from a hydrogen, a $C_1$-$C_{60}$ alkyl group, a $C_2$-$C_{60}$ alkenyl group, a $C_2$-$C_{60}$ aryl group, and a $C_1$-$C_{60}$ heteroaryl group);

$L_{501}$ to $L_{503}$ may be the same as defined in connection with $L_{201}$;

$R_{501}$ and $R_{502}$ may each independently be selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group;

xd1 to xd3 may each independently be selected from 0, 1, 2, and 3; and xb4 may be selected from 1, 2, 3, and 4.

An amount of the dopant in the emission layer may be, e.g., in a range of about 0.01 to about 15 parts by weight, based on 100 parts by weight of the host.

A thickness of the emission layer may be in a range of about 100 Å to about 1,000 Å, e.g., about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer (ETL), and an electron injection layer.

For example, the electron transport region may have a structure of electron transport layer/electron injection layer or a structure of hole blocking layer/electron transport layer/electron injection layer, wherein layers of each structure are sequentially stacked from the emission layer in the stated order.

In an implementation, the organic layer 150 of the organic light-emitting device may include the electron transport region between the emission layer and the second electrode 190, and the electron transport region may include the condensed cyclic compound represented by Formula 1.

The electron transport region may include a hole blocking layer. The hole blocking layer may be formed, when the emission layer includes a phosphorescent dopant, to help prevent diffusion of excitons or holes into an electron transport layer.

When the electron transport region includes a hole blocking layer, the hole blocking layer may be formed on the emission layer by using various methods, such as vacuum deposition, spin coating casting, a LB method, ink-jet printing, laser-printing, or laser-induced thermal imaging. When the hole blocking layer is formed by vacuum deposition or spin coating, deposition and coating conditions for the hole blocking layer may be determined by referring to the deposition and coating conditions for the hole injection layer.

The hole blocking layer may include, e.g., at least one of BCP and Bphen.

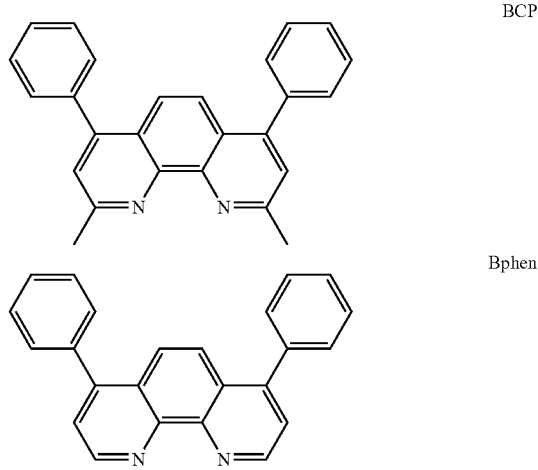

BCP

Bphen

A thickness of the hole blocking layer may be in a range of about 20 Å to about 1,000 Å, e.g., about 30 Å to about 300 Å. When the thickness of the hole blocking layer is within these ranges, the hole blocking layer may have improved hole blocking ability without a substantial increase in driving voltage.

The electron transport region may include an electron transport layer. The electron transport layer may be formed on the emission layer or the hole blocking layer by using various methods, such as vacuum deposition, spin coating casting, a LB method, ink-jet printing, laser-printing, or laser-induced thermal imaging. When an electron transport layer is formed by vacuum deposition or spin coating, deposition and coating conditions for the electron transport layer may be determined by referring to the deposition and coating conditions for the hole injection layer.

In an implementation, the organic layer 150 of the organic light-emitting device may include an electron transport region between the emission layer and the second electrode 190. The electron transport region may include at least one selected from an electron transport layer and an electron injection layer.

The electron transport layer may further include at least one selected from BCP, Bphen, Alq₃, BAlq, and NTAZ.

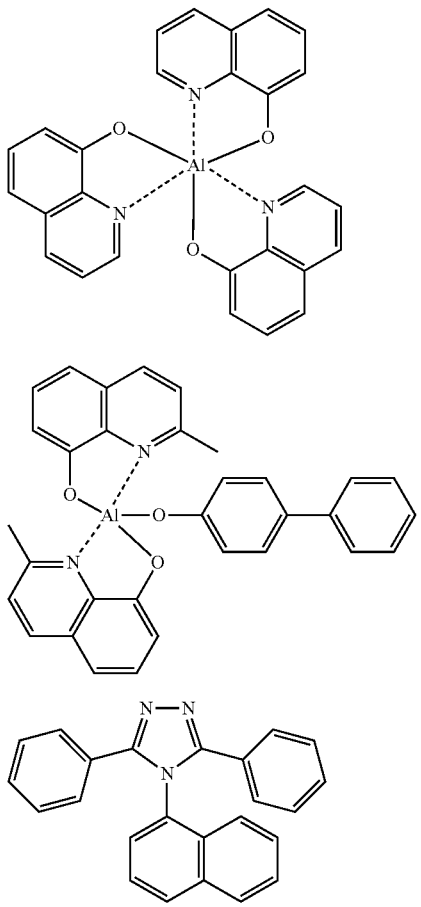

Alq₃

BAlq

NTAZ

In an implementation, the electron transport layer may include at least one compound selected from a compound represented by Formula 601 and a compound represented by Formula 602 illustrated below.

$$Ar_{601}-[(L_{601})_{xe1}-E_{601}]_{xe2}$$  <Formula 601>

In Formula 601, $Ar_{601}$ may be selected from a naphthalene, a heptalene, a fluorenene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene group, a heptalene group, a fluorenene group, a spiro-fluorenene group, a benzofluorenene group, a dibenzofluorenene group, a phenalene group, a phenanthrene group, a anthracene group, a fluoranthene group, a triphenylene group, a pyrene group, a chrysene group, a naphthacene group, a picene group, a perylene group, a pentaphene group, and an indenoanthracene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (wherein $Q_{301}$ to $Q_{303}$ are each independently selected from a hydrogen, a $C_1$-$C_{60}$ alkyl group, a $C_2$-$C_{60}$ alkenyl group, a $C_2$-$C_{60}$ aryl group, and a $C_1$-$C_{60}$ heteroaryl group);

$L_{601}$ may be the same as explained in connection with $L_{201}$;

$E_{601}$ may be selected from a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a furinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

xe1 may be selected from 0, 1, 2, and 3; and
xe2 may be selected from 1, 2, 3, and 4.

<Formula 602>

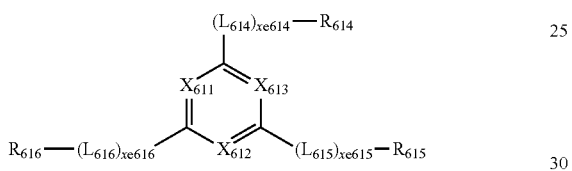

In Formula 602, $X_{611}$ may be N or C-$(L_{611})_{xe611}$-$R_{611}$, $X_{612}$ may be N or C-$(L_{612})_{xe612}$-$R_{612}$, $X_{613}$ may be N or C-$(L_{613})_{xe613}$-$R_{613}$ and, at least one of $X_{611}$ to $X_{613}$ may be N;

$L_{611}$ to $L_{616}$ may be the same as explained in connection with $L_{201}$;

$R_{611}$ to $R_{616}$ may each independently be selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 may each independently be selected from 0, 1, 2, and 3.

The compound represented by Formula 601 and the compound represented by Formula 602 may each be selected from Compounds ET1 to ET15 illustrated below.

ET1

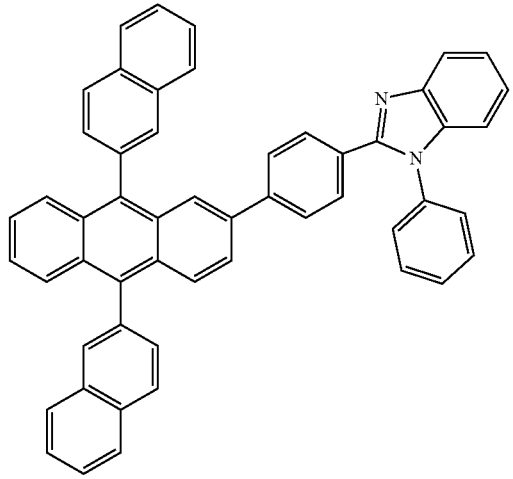

ET2

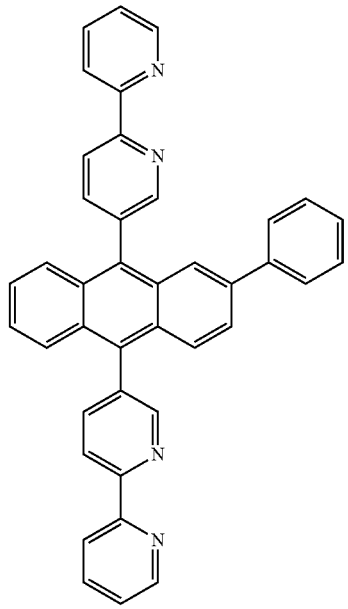

ET3
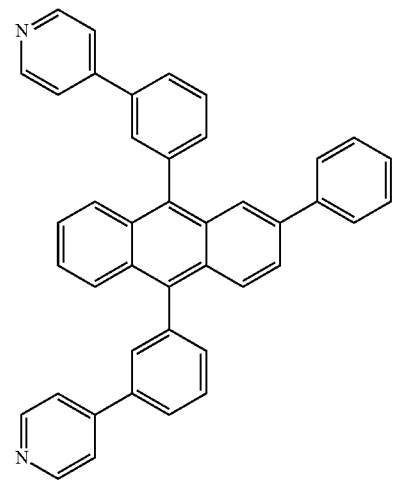
ET4
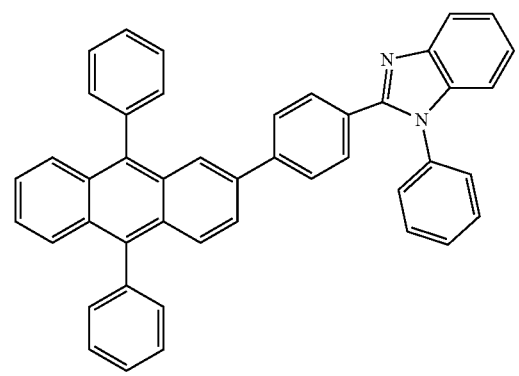
ET5
ET6
ET7
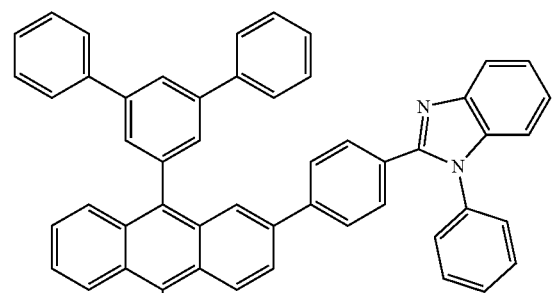
ET8
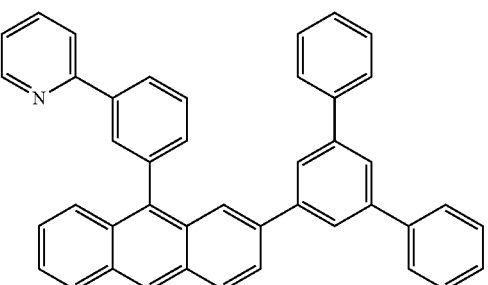
ET9
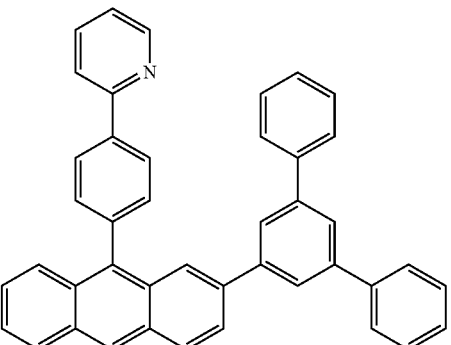

-continued

ET10
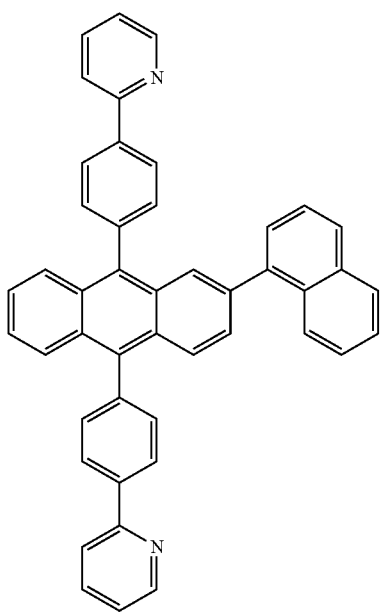

ET11
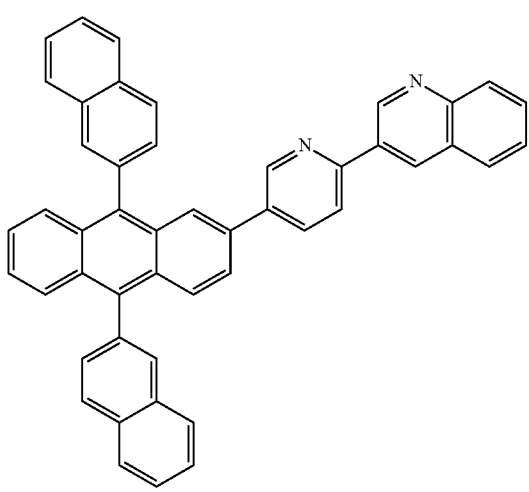

ET12
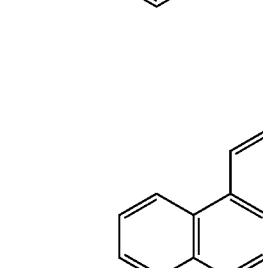
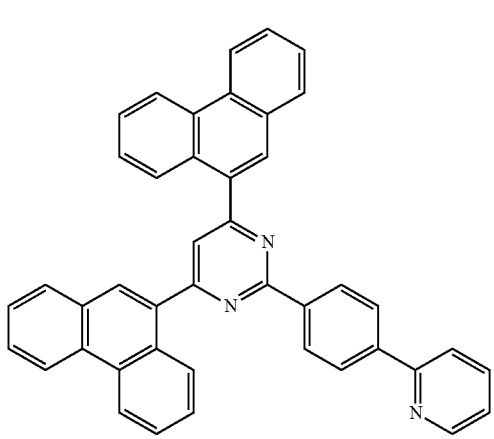

-continued

ET13
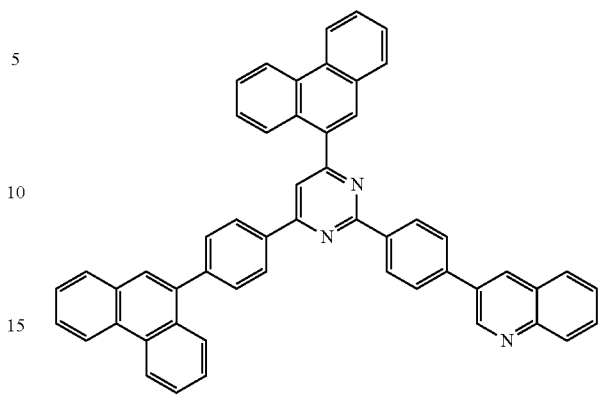

ET14
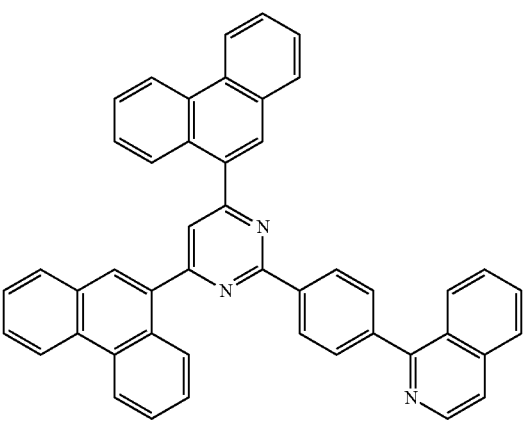

ET15
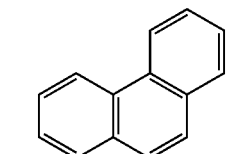
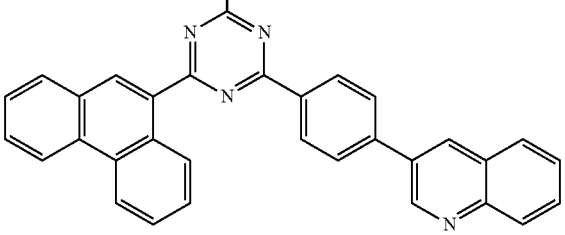

A thickness of the electron transport layer may be in a range of about 100 Å to about 1,000 Å, e.g., about 150 Å to about 500 Å. When the thickness of the electron transport layer is within the range described above, the electron transport layer may have satisfactory electron transport characteristics without a substantial increase in driving voltage.

In an implementation, the electron transport layer may further include, in addition to the materials described above, a metal-containing material.

The metal-containing material may include a Li complex. The Li complex may include, e.g., Compound ET-D1 (lithium quinolate, LiQ) or ET-D2.

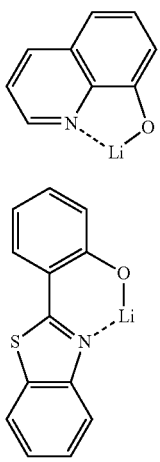

ET-D1

ET-D2

The electron transport region may include an electron injection layer that allows electrons to be easily provided from the second electrode 190.

The electron injection layer may be formed on the electron transport layer by using various methods, such as vacuum deposition, spin coating casting, a LB method, ink-jet printing, laser-printing, or laser-induced thermal imaging. When an electron injection layer is formed by vacuum deposition or spin coating, deposition and coating conditions for the electron injection layer may be determined by referring to the deposition and coating conditions for the hole injection layer.

The electron injection layer may include at least one selected from, LiF, NaCl, CsF, Li$_2$O, BaO, and LiQ.

A thickness of the electron injection layer may be in a range of about 1 Å to about 100 Å, e.g., about 3 Å to about 90 Å. When the thickness of the electron injection layer is within the range described above, the electron injection layer may have satisfactory electron injection characteristics without a substantial increase in driving voltage.

The second electrode 190 may be disposed on the organic layer 150 having such a structure. The second electrode 190 may be a cathode that is an electron injection electrode, and in this regard, a material for forming the second electrode 190 may be a material having a low work function, and such a material may be metal, alloy, an electrically conductive compound, or a mixture thereof. Examples of the second electrode 190 material may include lithium (Li), magnesium (Mg), aluminum (Al), aluminum-lithium (Al—Li), calcium (Ca), magnesium-indium (Mg—In), or magnesium-silver (Mg—Ag). In an implementation, the material for forming the second electrode 190 may include ITO or IZO. The second electrode 190 may be a reflective electrode, a semi-transmissive electrode, or a transmissive electrode.

A $C_1$-$C_{60}$ alkyl group used herein refers to a linear or branched aliphatic hydrocarbon monovalent group having 1 to 60 carbon atoms, and detailed examples thereof are a methyl group, an ethyl group, a propyl group, an isobutyl group, a sec-butyl group, a ter-butyl group, a pentyl group, an iso-amyl group, and a hexyl group. A $C_1$-$C_{60}$ alkylene group used herein refers to a divalent group having the same structure as the $C_1$-$C_{60}$ alkyl group.

A $C_1$-$C_{60}$ alkoxy group used herein refers to a monovalent group represented by —OA$_{101}$ (wherein A$_{101}$ is the $C_1$-$C_{60}$ alkyl group), and detailed examples thereof are a methoxy group, an ethoxy group, and an isopropyloxy group.

A $C_2$-$C_{60}$ alkenyl group used herein refers to a hydrocarbon group formed by substituting at least one carbon double bond in the middle or terminal of the $C_2$-$C_{60}$ alkyl group, and detailed examples thereof are an ethenyl group, a prophenyl group, and a butenyl group. A $C_2$-$C_{60}$ alkylene group used herein refers to a divalent group having the same structure as the $C_2$-$C_{60}$ alkyl group.

A $C_2$-$C_{60}$ alkynyl group used herein refers to a hydrocarbon group formed by substituting at least one carbon trip bond in the middle or terminal of the $C_2$-$C_{60}$ alkyl group, and detailed examples thereof are an ethynyl group, and a propynyl group. A $C_2$-$C_{60}$ alkylene group used herein refers to a divalent group having the same structure as the $C_2$-$C_{60}$ alkyl group.

A $C_3$-$C_{10}$ cycloalkyl group used herein refers to a monovalent hydrocarbon monocyclic group having 3 to 10 carbon atoms, and detailed examples thereof are a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_1$-$C_{10}$ heterocycloalkyl group used herein refers to a monovalent monocyclic group having at least one hetero atom selected from N, O, P, and S as a ring-forming atom and 1 to 10 carbon atoms, and detailed examples thereof are a tetrahydrofuranyl group, and a tetrahydrothiophenyl group. A $C_1$-$C_{10}$ heterocycloalkylene group used herein refers to a divalent group having the same structure as the $C_1$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof and does not have aromaticity, and detailed examples thereof are a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_1$-$C_{10}$ heterocycloalkenyl group used herein refers to a monovalent monocyclic group that has at least one hetero atom selected from N, O, P, and S as a ring-forming atom, 1 to 10 carbon atoms, and at least one double bond in its ring. Detailed examples of the $C_1$-$C_{10}$ heterocycloalkenyl group are a 2,3-hydrofuranyl group and a 2,3-hydrothiophenyl group. A $C_1$-$C_{10}$ heterocycloalkenylene group used herein refers to a divalent group having the same structure as the $C_1$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include 2 or more rings, the rings may be fused to each other.

A $C_1$-$C_{60}$ heteroaryl group used herein refers to a monovalent group having a carboncyclic aromatic system that has at least one hetero atom selected from N, O, P, and S as a ring-forming atom, and 1 to 60 carbon atoms. A $C_1$-$C_{60}$ heteroarylene group used herein refers to a divalent group having a carbocyclic aromatic system that has at least one hetero atom selected from N, O, P, and S as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include 2 or more rings, the rings may be fused to each other.

A $C_6$-$C_{60}$ aryloxy group used herein indicates —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

A monovalent non-aromatic condensed polycyclic group used herein refers to a monovalent group (for example, having 8 to 60 carbon atoms) that has 2 or more rings condensed to each other, only carbon atoms as a ring forming atom, and non-aromacity in the entire molecular structure. A detailed example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group used herein refers to a monovalent group (for example, having 1 to 60 carbon atoms) that has 2 or more rings condensed to each other, has a heteroatom selected from N, O P, and S, other than carbon atoms, as a ring forming atom, and has non-aromacity in the entire molecular structure. An example of the monovalent non-aromatic condensed heteropolycyclic group is a carbazolyl group. A divalent non-aromatic condensed heteropolycyclic group used herein refers to a divalent group having the same structure as the monovalent non-aromatic condensed heteropolycyclic group.

At least one substituent of the substituted $C_3$-$C_{10}$ cycloalkylene group, substituted $C_3$-$C_{10}$ cycloalkenylene group, substituted $C_6$-$C_{60}$ arylene group, substituted a divalent non-aromatic condensed polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_6$-$C_{60}$ aryl group, substituted $C_6$-$C_{60}$ aryloxy group, substituted $C_6$-$C_{60}$ arylthio group, and substituted monovalent non-aromatic condensed polycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, and a monovalent non-aromatic condensed polycyclic group;

a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, and a monovalent non-aromatic condensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$;

wherein $Q_1$ to $Q_7$, $Q_{11}$ to $Q_{17}$, $Q_{21}$ to $Q_{27}$, and $Q_{31}$ to $Q_{37}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_6$-$C_{60}$ aryl group, and a monovalent non-aromatic condensed polycyclic group.

For example, at least one substituent of the substituted $C_3$-$C_{10}$ cycloalkylene group, substituted $C_3$-$C_{10}$ cycloalkenylene group, substituted $C_6$-$C_{60}$ arylene group, substituted a divalent non-aromatic condensed polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_6$-$C_{60}$ aryl group, substituted $C_6$-$C_{60}$ aryloxy group, substituted $C_6$-$C_{60}$ arylthio group, and substituted monovalent non-aromatic condensed polycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, —$N(Q_{11})(Q_{12})$, —$Si(Q_{13})(Q_{14})(Q_{15})$, and —$B(Q_{16})(Q_{17})$;

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group;

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$;

wherein $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group.

The term "Ph" used herein refers to a phenyl group, the term "Me" used herein refers to a methyl group, the term "Et" used herein refers to an ethyl group, and the term "ter-Bu" or "Bu" used herein refers to a tert-butyl group.

Hereinafter, an organic light-emitting device according to an embodiment will be described in detail with reference to Synthesis Examples and Examples. The wording "B was used instead of A" used in describing Synthesis Examples means that a molar equivalent of A was identical to a molar equivalent of B.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Example

Synthesis Example 1

Synthesis of Compound 1

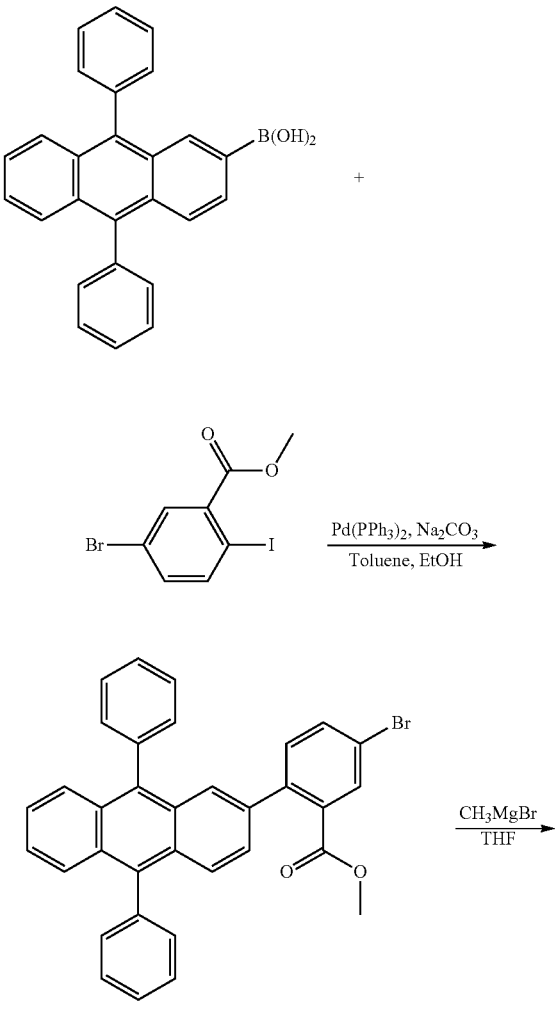

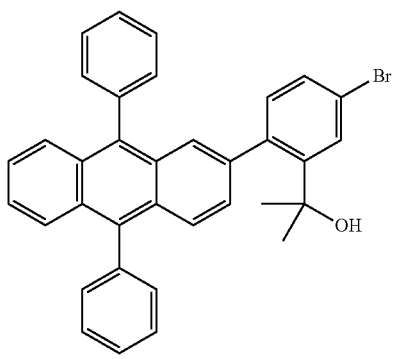

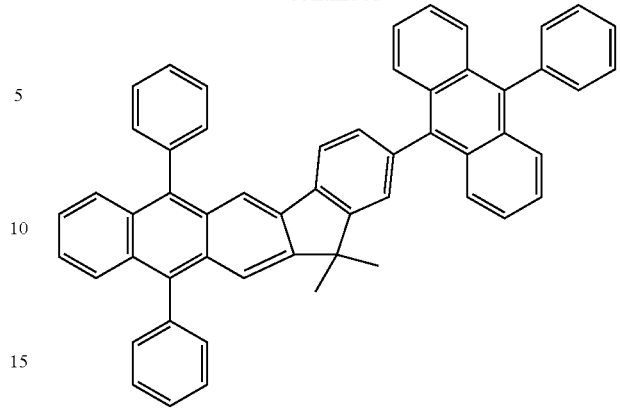

Compound 1

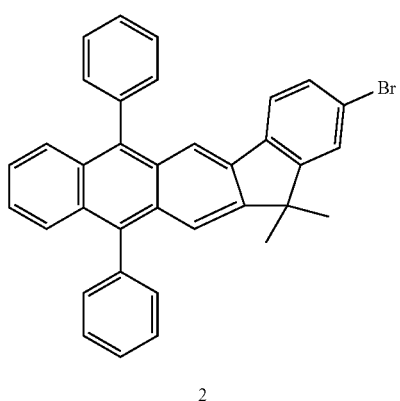

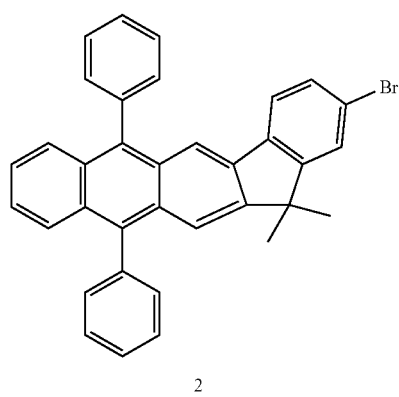

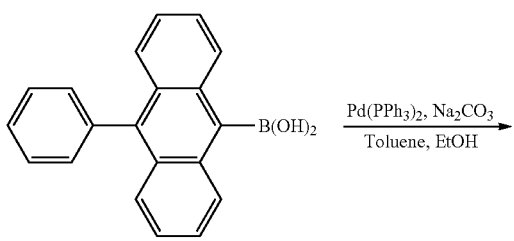

Synthesis of Intermediate 1

2.01 g (1 eq, 5.89 mmol) of methyl 5-bromo-2-iodobenzoate, 2.27 g (1.03 eq, 6.07 mmol) of 9,10-diphenylanthracen-2-ylboronic acid, and 0.28 g (0.04 eq, 0.24 mmol) of tetrakis(triphenylphosphine)palladium(0) were added to a reaction container, and then vacuum-dried and filled with nitrogen gas. 17.7 ml of toluene was added to the reaction container to dissolve these compounds, and then, 8.8 ml of ethanol and 8.8 ml (3 eq, 17.69 mmol) of 2.0M aqueous sodium carbonate solution were added thereto, and the result was stirred while refluxing at a temperature of 120° C. for 3 hours. When the reaction stopped, the reaction product was washed with distilled water, and an organic layer was extracted therefrom using ethyl acetate. The organic layer was dried using magnesium sulfate and filtered, and then a solvent was removed therefrom by evaporation. Then, the result was recrystallized using dichloromethane and methanol to obtain 2.03 g (yield of 62%) of Intermediate 1.

$^1$H-NMR: 8.20 (s, 1H), 8.13 (s, 1H), 7.97 (d, 1H), 7.91 (s, 2H), 7.70 (d, 1H), 7.61 (d, 1H), 7.48 (m, 5H), 7.39 (dd, 2H), 7.32 (t, 4H), 7.22 (t, 2H), 3.88 (m, 3H). APCI-MS (m/z): 543 [M$^+$]

Synthesis of Intermediate 2

5.34 g (1 eq, 59.83 mmol) of Intermediate 1 was added to a reaction container, and then vacuum-dried and filled with nitrogen gas. 70 ml of THF was added to the reaction container, and then, 5 ml (3.0 eq, 0.03 mol) of methylmagnesium bromide (3.0M) was slowly added dropwise thereto. The reaction solution was extracted using ethyl ether and dried, and then, the result was added to a flask, and 6 ml of methane sulfonic acid was added thereto, and the mixture was stirred at ambient temperature. When the reaction stopped, the reaction product was extracted using ethyl acetate, and then purified by column chromatography to obtain 1.6 g (yield of 70%) of Intermediate 2.

$^1$H-NMR: 7.77 (d, 1H), 7.69 (d, 1H), 7.56 (m, 10H), 7.45 (m, 3H), 7.39 (dd, 2H), 7.28 (dd, 2H), 0.93 (s, 6H). APCI-MS (m/z): 524 [M$^+$]

Synthesis of Compound 1

0.7 g (1 eq, 1.33 mmol) of Intermediate 2, 0.44 g (1.1 eq, 1.46 mmol) of 9-phenylanthracene-10-ylboronic acid, and 0.06 g (0.04 eq, 0.05 mmol) of tetrakis(triphenylphosphine) palladium (0) were added to a reaction container and then, vacuum-dried and filled with nitrogen gas. 8 ml of toluene was added to the reaction container to dissolve these compounds, and then, 4 ml of ethanol and 4 ml (3 eq, 3.99 mmol) of 2.0 M aqueous sodium carbonate solution were added thereto, and the result was stirred while refluxing at a temperature of 120° C. for 3 hours. When the reaction stopped, the reaction product was washed with distilled water, and an organic layer was extracted therefrom using ethyl acetate. The organic layer was dried using magnesium sulfate and filtered, and then a solvent was removed therefrom by evaporation. Then, the result was purified by column chromatography to obtain 0.52 g (yield of 60%) of Compound 1.

$^1$H-NMR: 7.88 (m, 4H), 7.76 (m, 2H), 7.69 (m, 2H), 7.60 (m, 9H), 7.50 (m, 8H), 7.42 (dd, 2H), 7.30 (td, 5H), 1.03 (s, 6H). APCI-MS (m/z): 698 [M$^+$]

Synthesis Example 2

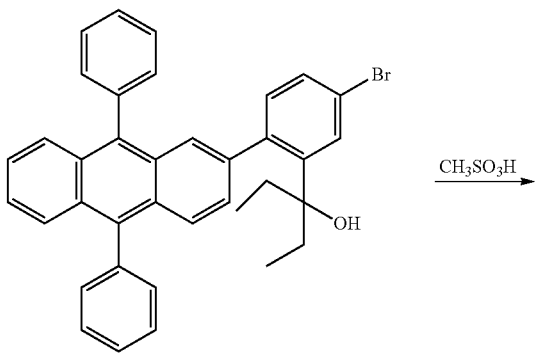

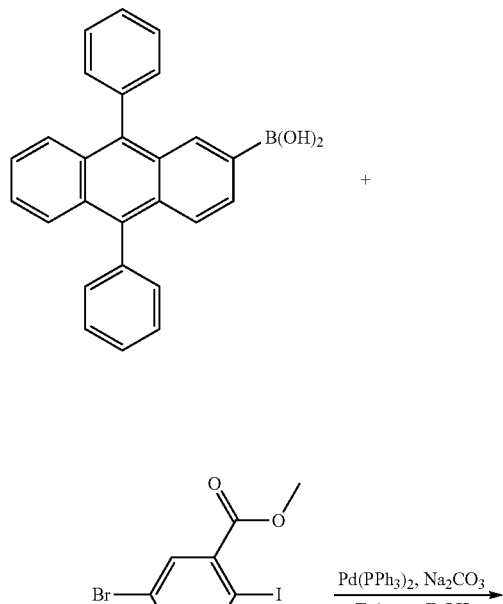

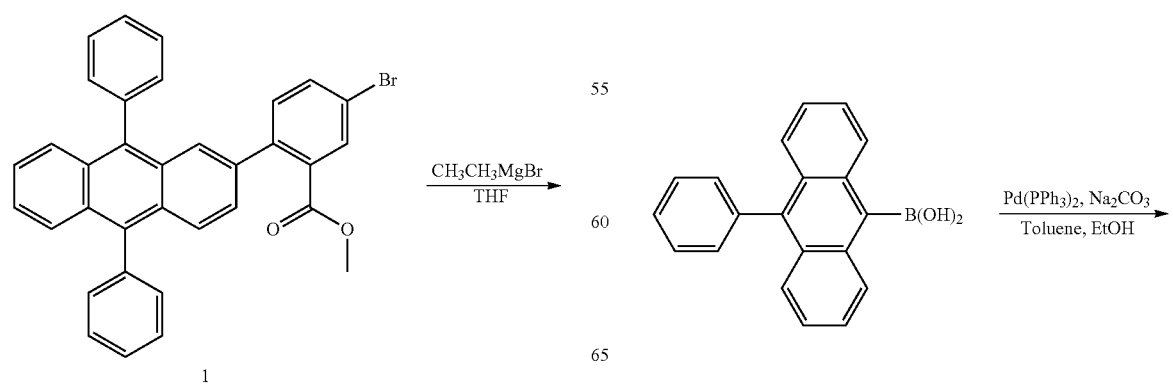

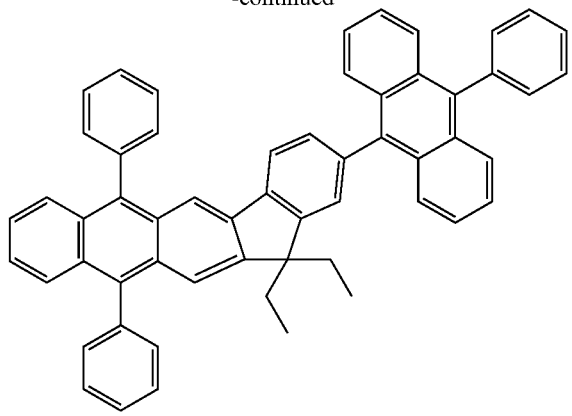

Compound 8

Synthesis of Intermediate 3

5.34 g (1 eq, 59.83 mmol) of Intermediate 1 (from Synthesis Example 1) was added to a reaction container, and then vacuum-dried and filled with nitrogen gas. 70 ml of THF was added to the reaction container, and then, 5 ml (3.0 eq, 0.03 mol) of ethylmagnesium bromide (3.0 M) was slowly added dropwise thereto. The reaction solution was extracted using ethyl ether and dried, and then the result was added to a flask, and 6 ml of methane sulfate was added thereto, and the mixture was stirred at ambient temperature. When the reaction stopped, the reaction product was extracted using ethyl acetate, and then purified by column chromatography to obtain 1.6 g (yield of 70%) of Intermediate 3.

$^1$H-NMR: 8.07 (s, 1H), 7.91 (s, 2H), 7.95 (d, 1H), 7.76 (s, 1H), 7.78 (s, 1H), 7.61 (t, 1H), 7.48 (d, 4H), 7.39 (t, 2H), 7.32 (t, 4H), 7.22 (t, 2H), 1.91 (s, 6H). APCI-MS (m/z): 552 [M$^+$]

Synthesis of Compound 8

0.7 g (1 eq, 1.33 mmol) of Intermediate 3, 0.44 g (1.1 eq, 1.46 mmol) of 9-phenylanthracene-10-ylboronic acid, and 0.06 g (0.04 eq, 0.05 mmol) of tetrakis(triphenylphosphine)palladium (0) were added to a reaction container and then, vacuum-dried and filled with nitrogen gas. 8 ml of toluene was added to the reaction container to dissolve these compounds, and then, 4 ml of ethanol and 4 ml (3 eq, 3.99 mmol) of 2.0 M aqueous sodium carbonate solution were added thereto, and the result was stirred while refluxing at a temperature of 120° C. for 3 hours. When the reaction stopped, the reaction product was washed with distilled water, and an organic layer was extracted therefrom using ethyl acetate. The organic layer was dried using magnesium sulfate and filtered, and then a solvent was removed therefrom by evaporation. Then, the result was purified by column chromatography to obtain 0.48 g (yield of 57%) of Compound 8.

$^1$H-NMR: 8.12 (d, 1H), 8.07 (s, 1H), 7.91 (m, 6H), 7.83 (s, 1H), 7.76 (s, 1H), 7.66 (d, 1H) 7.48 (d, 6H), 7.39 (td, 6H), 7.32 (t, 6H), 7.22 (t, 3H), 1.91 (t, 4H), 0.96 (d, 6H). APCI-MS (m/z): 726 [M$^+$

Synthesis Example 3

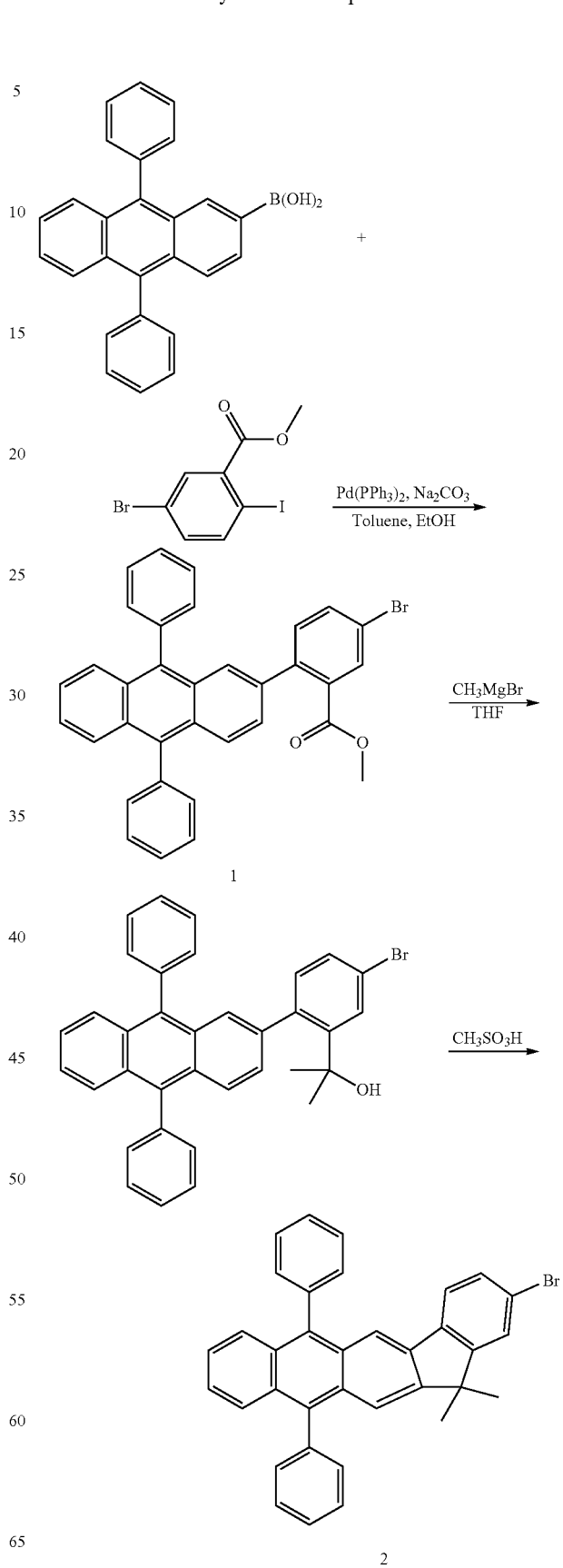

85
-continued

86
Synthesis Example 4

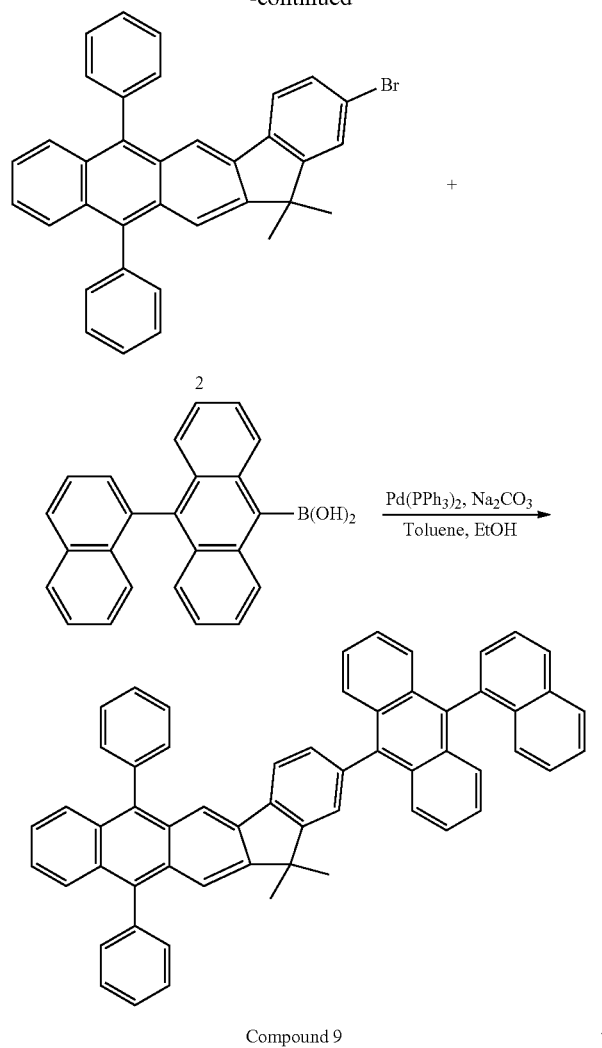

Compound 9

Synthesis of Compound 9

0.7 g (1 eq, 1.33 mmol) of Intermediate 2 (from Synthesis Example 1, above), 0.56 g (1.1 eq, 1.46 mmol) of 9-naphthylanthracene-10-ylboronic acid, and 0.06 g (0.04 eq, 0.05 mmol) of tetrakis(triphenylphosphine)palladium (0) were added to a reaction container and then, vacuum-dried and filled with nitrogen gas. 8 ml of toluene was added to the reaction container to dissolve these compounds, and then, 4 ml of ethanol and 4 ml (3 eq, 3.99 mmol) of 2.0 M aqueous sodium carbonate solution were added thereto, and the result was stirred while refluxing at a temperature of 120° C. for 3 hours. When the reaction stopped, the reaction product was washed with distilled water, and an organic layer was extracted therefrom using ethyl acetate. The organic layer was dried using magnesium sulfate and filtered, and then a solvent was removed therefrom by evaporation. Then, the result was purified by column chromatography to obtain 0.42 g (yield of 53%) of Compound 9.

$^1$H-NMR: 8.12 (d, 1H), 8.07 (s, 1H), 7.91 (m, 6H), 7.83 (s, 1H), 7.76 (s, 1H), 7.67 (d, 2H), 7.66 (d, 1H) 7.63 (d, 2H), 7.54 (d, 1H), 7.48 (d, 4H), 7.39 (td, 6H), 7.38 (d, 1H), 7.32 (t, 6H), 7.22 (t, 2H), 1.73 (t, 6H), 0.96 (d, 6H). APCI-MS (m/z): 749 [M$^+$]

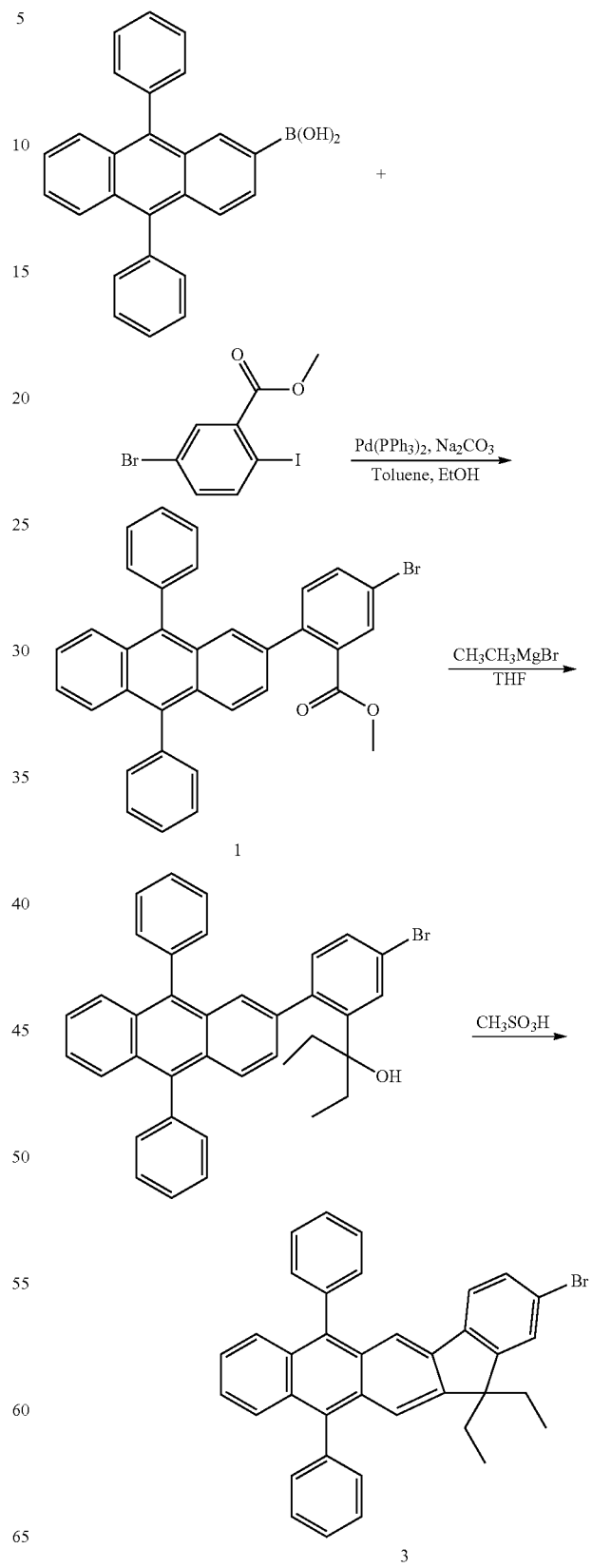

-continued

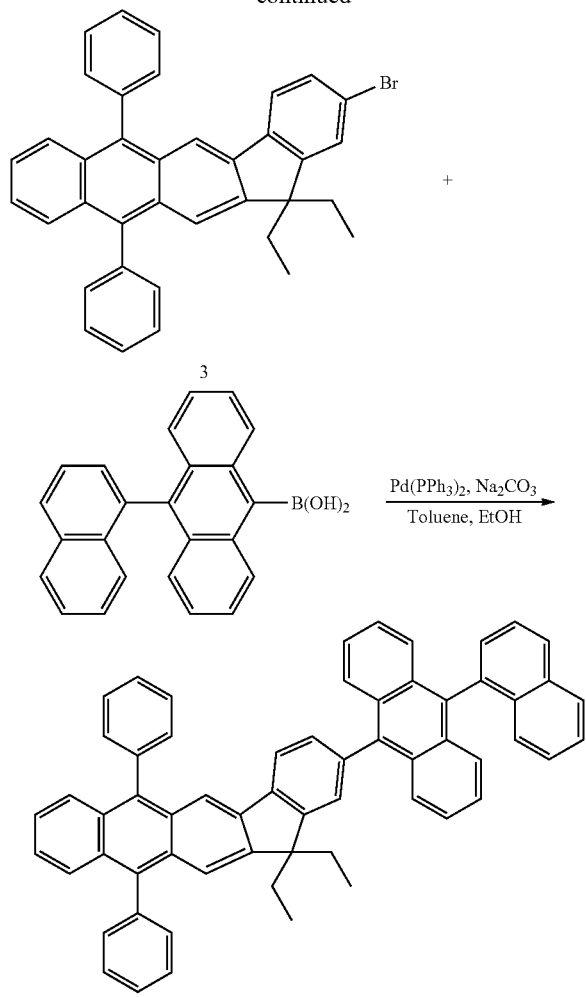

Compound 11

Synthesis of Compound 11

0.7 g (1 eq, 1.33 mmol) of Intermediate 3 (from Synthesis Example 2, above), 0.50 g (1.1 eq, 1.46 mmol) of 9-naphthylanthracene-10-ylboronic acid, and 0.06 g (0.04 eq, 0.05 mmol) of tetrakis(triphenylphosphine)palladium (0) were added to a reaction container and then, vacuum-dried and filled with nitrogen gas. 8 ml of toluene was added to the reaction container to dissolve these compounds, and then, 4 ml of ethanol and 4 ml (3 eq, 3.99 mmol) of 2.0 M aqueous sodium carbonate solution were added thereto, and the result was stirred while refluxing at a temperature of 120° C. for 3 hours. When the reaction stopped, the reaction product was washed with distilled water, and an organic layer was extracted therefrom using ethyl acetate. The organic layer was dried using magnesium sulfate and filtered, and then a solvent was removed therefrom by evaporation. Then, the result was purified by column chromatography to obtain 0.42 g (yield of 50%) of Compound 11.

$^1$H-NMR: 8.12 (d, 1H), 8.07 (s, 1H), 7.91 (m, 6H), 7.83 (s, 1H), 7.76 (s, 1H), 7.67 (d, 2H), 7.66 (d, 1H), 7.63 (d, 1H), 7.54 (d, 1H), 7.48 (d, 4H), 7.39 (td, 6H), 7.38 (t, 1H), 7.32 (t, 6H), 7.22 (t, 2H), 1.91 (t, 4H), 0.96 (d, 6H). APCI-MS (m/z): 777 [M$^+$]

Example 1

A ITO glass substrate (product of Corning Inc.) including an ITO layer having a thickness of 15 Ω/cm$^2$ (1,200 Å) was cut to a size of 50 mm×50 mm×0.7 mm, and then, sonicated with isopropyl alcohol and pure water, each for 5 minutes, and then, cleaned by exposure to ultraviolet irradiation for 30 minutes, and then to ozone. The resultant ITO glass substrate was mounted on a vacuum deposition device.

The 2-TNATA was deposited on the ITO glass substrate to form a hole injection layer having a thickness of 600 Å, NPB was deposited on the hole injection layer to form a hole transport layer having a thickness of 300 Å, and then, Compound 1(host) and F$_2$IrPIC(dopant) were co-deposited at a weight ratio of 98:2 on the hole transport layer to form an emission layer having a thickness of 300 Å.

Alq$_3$ was deposited on the emission layer to form an electron transport layer having a thickness of 300 Å, LiQ was deposited on the electron transport layer to form an electron injection layer having a thickness of 10 Å, and then, Al was deposited on the electron injection layer to form a cathode having a thickness of 3,000 Å, thereby completing the manufacture of an organic light-emitting device.

Example 2

An organic light-emitting device was manufactured in the same manner as in Example 1, except that in forming an emission layer, as a host, Compound 8 was used instead of Compound 1.

Example 3

An organic light-emitting device was manufactured in the same manner as in Example 1, except that in forming an emission layer, as a host, Compound 9 was used instead of Compound 1.

Example 4

An organic light-emitting device was manufactured in the same manner as in Example 1, except that in forming an emission layer, as a host, Compound 11 was used instead of Compound 1.

Comparative Example 1

An organic light-emitting device was manufactured in the same manner as in Example 1, except that in forming an emission layer, as a host, Compound A illustrated below was used instead of Compound 1.

<Compound A>

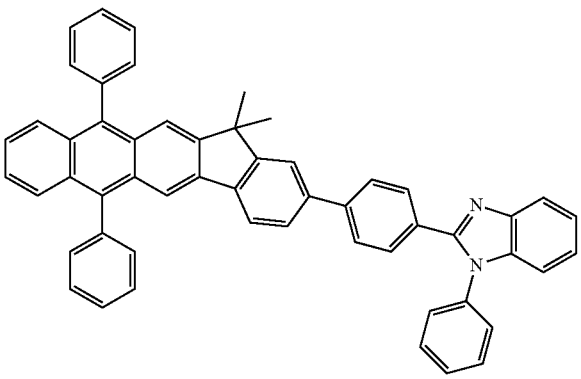 [SMILES: CC1(C)c2cc(-c3ccc(-c4nc5ccccc5n4-c4ccccc4)cc3)ccc2-c2cc3c(-c4ccccc4)c4ccccc4c(-c4ccccc4)c3cc21]

Comparative Example 2

An organic light-emitting device was manufactured in the same manner as in Example 1, except that in forming an emission layer, as a host, Compound B illustrated below was used instead of Compound 1.

<Compound B>

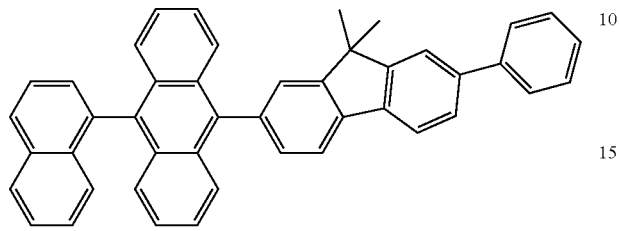

Evaluation Example 1

The driving voltage, current density, brightness, efficiency, and half-lifespan of the organic light-emitting devices manufactured according to Examples 1 to 4, and Comparative Examples 1 and 2 were measured by using Kethley SMU 236 and a brightness photometer PR650, and results thereof are shown in Table 1. The half-lifespan is a period of time that is taken until the brightness of the organic light-emitting device was 90% of initial brightness.

TABLE 1

| | Emission layer host | Driving voltage (V) | Current Density (mA/cm$^2$) | Brightness (cd/m$^2$) | efficiency (cd/A) | Emission color | Half lifespan (hr @100 mA/cm$^2$) |
|---|---|---|---|---|---|---|---|
| Example 1 | Compound 1 | 4.2 | 11.9 | 709 | 7.0 | Blue | 356 |
| Example 2 | Compound 8 | 4.4 | 12.3 | 560 | 6.2 | Blue | 320 |
| Example 3 | Compound 9 | 4.5 | 14.9 | 573 | 4.8 | Blue | 365 |
| Example 4 | Compound 11 | 4.4 | 13.8 | 587 | 5.4 | Blue | 422 |
| Comparative Example 1 | Compound A | 4.6 | 16.4 | 595 | 4.8 | Green | 397 |
| Comparative Example 2 | Compound B | 4.8 | 15.9 | 607 | 5.2 | Blue | 349 |

From Table 1, it may be that the driving voltage, brightness, efficiency, and half-lifespan of the organic light-emitting devices manufactured according to Examples 1 to 4 were higher than the driving voltage, brightness, efficiency, and half-lifespan of the organic light-emitting devices manufactured according to Comparative Examples 1 and 2.

An organic light-emitting device including the compound according to an embodiment may have a low driving voltage, high efficiency, high brightness, and long lifespan.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:
1. An organic light-emitting device, comprising:
a first electrode;
a second electrode facing the first electrode; and
an organic layer between the first electrode and the second electrode and including an emission layer, wherein the emission layer includes a condensed cyclic compound represented by Formula 1(1) or Formula 1(2) below:

<Formula 1(1)>

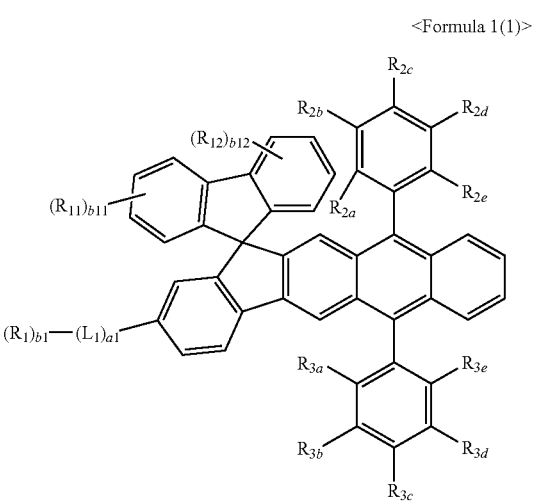

-continued

<Formula 1(2)>

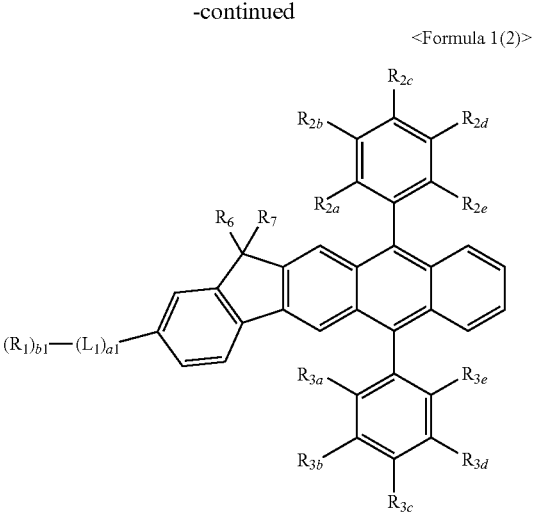

wherein, in Formulae 1(1) and 1(2), $L_1$ is selected from a substituted or unsubstituted $C_3$-$C_{10}$ cycloalkylene group, a substituted or unsubstituted $C_3$-$C_{10}$ cycloalkenylene group, a substituted or unsubstituted $C_{12}$-$C_{60}$ polycyclic arylene group, or a substituted or unsubstituted divalent non-aromatic condensed polycyclic group;

a1 is 1;

$R_1$, $R_6$, $R_7$, $R_{11}$, and $R_{12}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group, —N($Q_1$)($Q_2$), —Si($Q_3$)($Q_4$)($Q_5$), or —B($Q_6$)($Q_7$);

$R_{2a}$ to $R_{2e}$ and $R_{3a}$ to $R_{3e}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted monovalent non-aromatic condensed polycyclic group, —N($Q_1$)($Q_2$), —Si($Q_3$)($Q_4$)($Q_5$), or —B($Q_6$)($Q_7$);

b1, b11, and b12 are each independently an integer selected from 1, 2, or 3;

at least one substituent of the substituted $C_3$-$C_{10}$ cycloalkylene group, substituted $C_3$-$C_{10}$ cycloalkenylene group, substituted $C_{12}$-$C_{60}$ polycyclic group, substituted a divalent non-aromatic condensed polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_6$-$C_{60}$ aryl group, substituted $C_6$-$C_{60}$ aryloxy group, substituted $C_6$-$C_{60}$ arylthio group, and substituted monovalent non-aromatic condensed polycyclic group is selected from:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, —N($Q_{11}$)($Q_{12}$), —Si($Q_{13}$)($Q_{14}$)($Q_{15}$), or —B($Q_{16}$)($Q_{17}$);

a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, or a monovalent non-aromatic condensed polycyclic group;

a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, and a monovalent non-aromatic condensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, —N($Q_{21}$)($Q_{22}$), —Si($Q_{23}$)($Q_{24}$)($Q_{25}$), or —B($Q_{26}$)($Q_{27}$); or —N($Q_{31}$)($Q_{32}$), —Si($Q_{33}$)($Q_{34}$)($Q_{35}$), or —B($Q_{36}$)($Q_{37}$);

wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_6$-$C_{60}$ aryl group, or a monovalent non-aromatic condensed polycyclic group.

2. The organic light-emitting device as claimed in claim 1, wherein:

$R_1$, $R_{11}$, and $R_{12}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted monovalent non-aromatic condensed polycyclic group, or —Si($Q_3$)($Q_4$)($Q_5$), and $R_6$ and $R_7$ are each independently selected from a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, or a substituted or unsubstituted monovalent non-aromatic condensed polycyclic group.

3. The organic light-emitting device as claimed in claim 1, wherein $R_1$ is selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, or a $C_1$-$C_{20}$ alkoxy group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, or an ovalenyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, or an ovalenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, or an ovalenyl group; or $Si(Q_3)(Q_4)(Q_5)$, in which $Q_3$ to $Q_5$ are each independently selected from a $C_1$-$C_{20}$ alkyl group, a $C_1$-$C_{20}$ alkoxy group, a phenyl group, or a naphthyl group.

4. The organic light-emitting device as claimed in claim 1, wherein $R_1$ is selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, or a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, or a chrysenyl group; or a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, or a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, or a chrysenyl group.

5. The organic light-emitting device as claimed in claim 1, wherein $R_6$ and $R_7$ are each independently selected from:

a $C_1$-$C_{20}$ alkyl group or a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, or a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, or a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, or a chrysenyl group.

6. The organic light-emitting device as claimed in claim 1, wherein:

$R_1$ is selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid and a salt thereof, a $C_1$-$C_{20}$ alkyl group, a $C_1$-$C_{20}$ alkoxyl group, or a group represented by one of Formulae 5-1 to 5-11 below; and $R_6$ and $R_7$ are each independently selected from a $C_1$-$C_{20}$ alkyl group, a $C_1$-$C_{20}$ alkoxy group, or a group represented by one of Formulae 5-1 to 5-11 below:

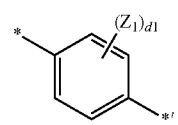

Formula 3-1

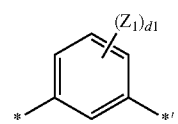

Formula 3-2

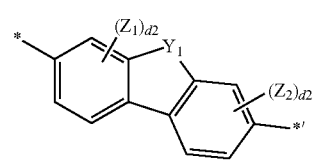

Formula 3-3

-continued

Formula 3-4
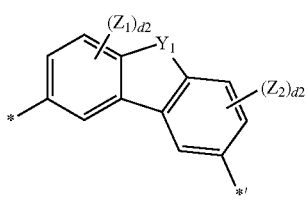

Formula 3-5
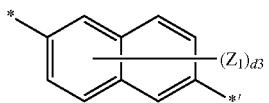

Formula 3-6
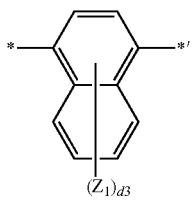

Formula 3-7
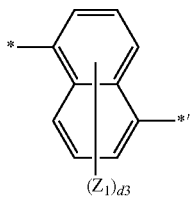

Formula 3-8
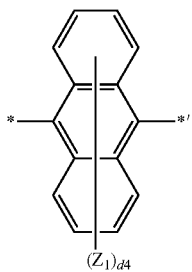

Formula 3-9
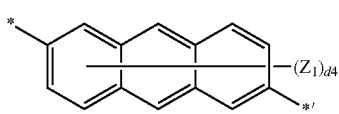

Formula 3-10
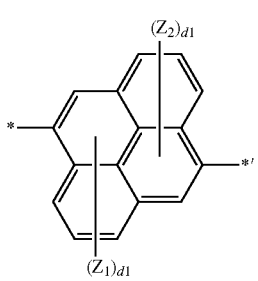

Formula 3-11
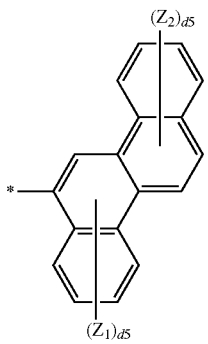

Formula 3-12
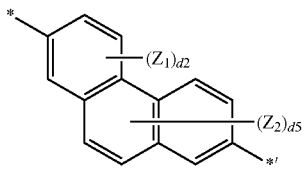

Formula 3-13
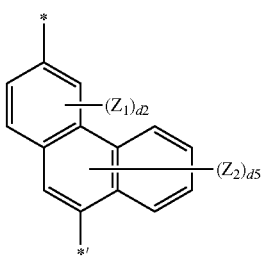

wherein, in Formulae 5-1 to 5-11, $Y_{31}$ is $C(Z_{33})(Z_{34})$;

$Z_{31}$ to $Z_{34}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spirofluorenyl group, a benzofluorenyl group, a dibenzofluorenyl group, a phenanthrenyl group, an anthracenyl group, a pyrenyl group, or a chrysenyl group, e1 is an integer selected from 1, 2, 3, 4, or 5, e2 is an integer selected from 1, 2, 3, 4, 5, 6, or 7, e3 is an integer selected from 1, 2, or 3, e4 is an integer selected from 1, 2, 3, or 4, e5 is an integer selected from 1, 2, 3, 4, or 5, e6 is an integer selected from 1, 2, 3, 4, 5, or 6, and * indicates a binding site to a neighboring atom.

7. The organic light-emitting device as claimed in claim 1, wherein:

$R_1$ is selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid and a salt thereof, a $C_1$-$C_{20}$ alkyl group, a $C_1$-$C_{20}$ alkoxyl group, or a group represented by one of Formulae 6-1 to 6-18 below;

$R_6$ and $R_7$ are each independently selected from a $C_1$-$C_{20}$ alkyl group, a $C_1$-$C_{20}$ alkoxy group, or a group represented by one of Formulae 6-1 to 6-18 below:

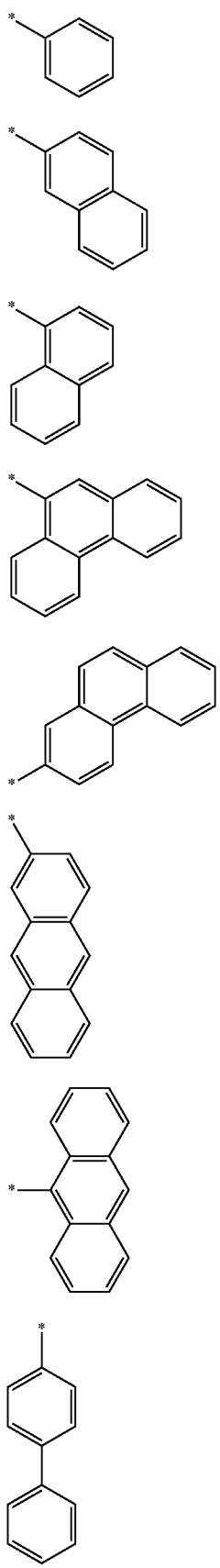
Formula 6-1
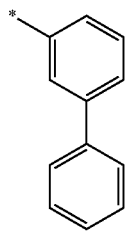
Formula 6-2
Formula 6-3
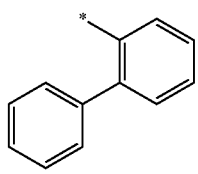
Formula 6-4
Formula 6-5
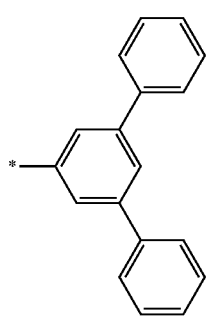
Formula 6-6
Formula 6-7
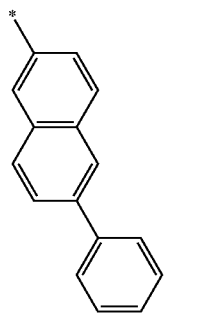
Formula 6-8
Formula 6-9
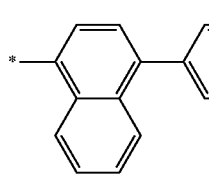
Formula 6-10
Formula 6-11
Formula 6-12
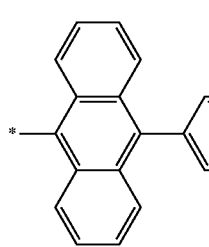
Formula 6-13
Formula 6-14

-continued

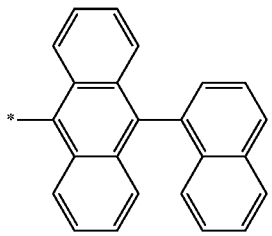
Formula 6-15

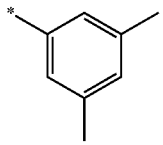
Formula 6-16

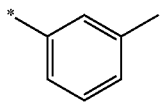
Formula 6-17

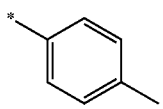
Formula 6-18 wherein * in Formulae 6-1 to 6-18 indicates a binding site to a neighboring atom.

8. The organic light-emitting device as claimed in claim 1, wherein:

$R_6$ and $R_7$ are each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, or a chrysenyl group; or a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, or a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, or a chrysenyl group.

9. The organic light-emitting device as claimed in claim 1, wherein a1 and b1 are both 1;

$L_1$ is a group represented by one of Formulae 4-9 to 4-15 below;

$R_1$, $R_6$, and $R_7$ are each independently selected from a $C_1$-$C_{20}$ alkyl group, a $C_1$-$C_{20}$ alkoxy group, or a group represented by one of Formulae 6-1 to 6-18 below:

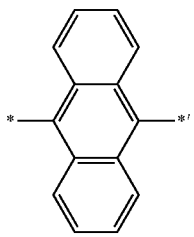
Formula 4-9

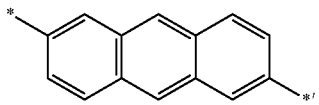
Formula 4-10

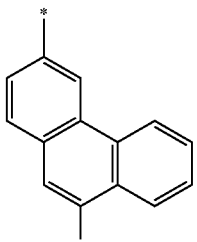
Formula 4-11

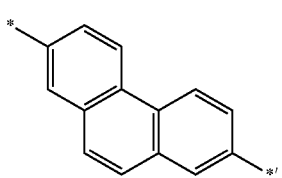
Formula 4-12

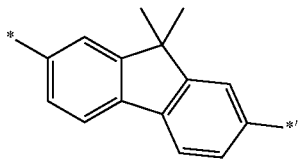
Formula 4-13

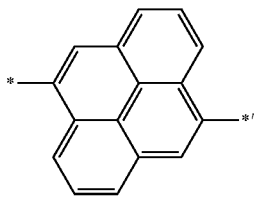
Formula 4-14

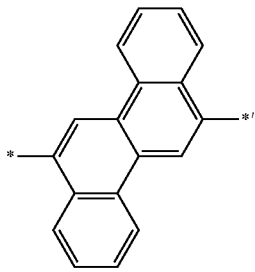
Formula 4-15

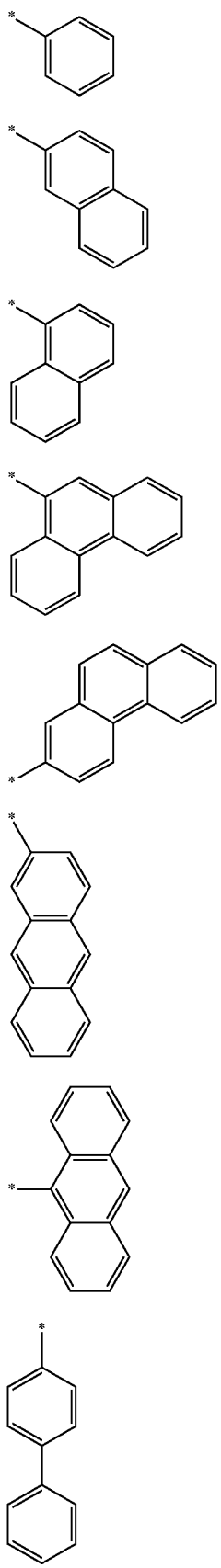
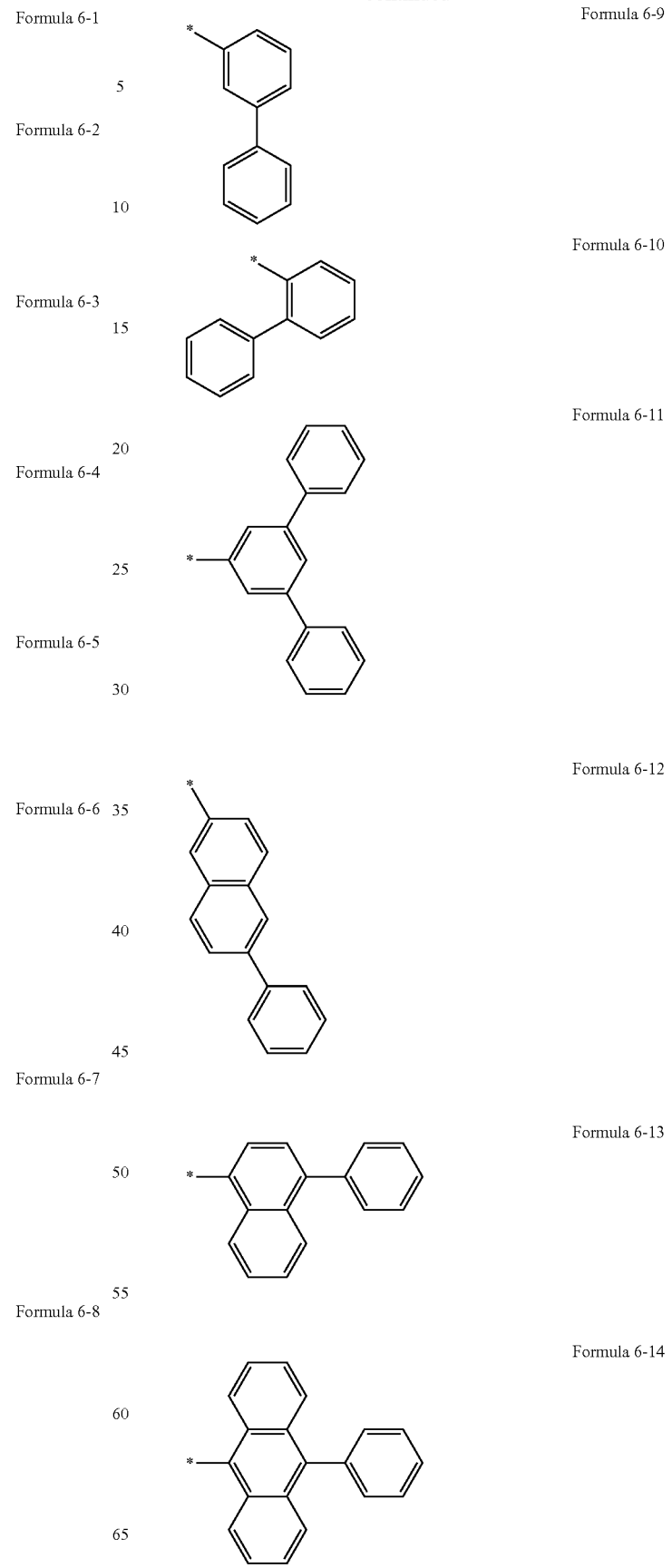

Formula 6-15
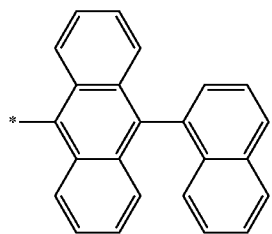
Formula 6-16
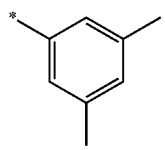
Formula 6-17
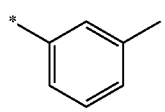
Formula 6-18
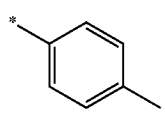
wherein * and *' in Formulae 4-9 to 4-15 indicate binding sites to a neighboring atom, and * in Formulae 6-1 to 6-18 indicate binding sites to a neighboring atom.
10. The organic light-emitting device as claimed in claim 1, wherein the condensed cyclic compound represented by Formula 1(1) or Formula 1(2) is one of Compounds 1 to 14 below:
1
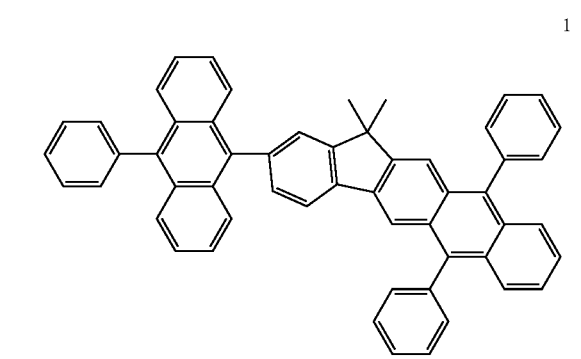
2
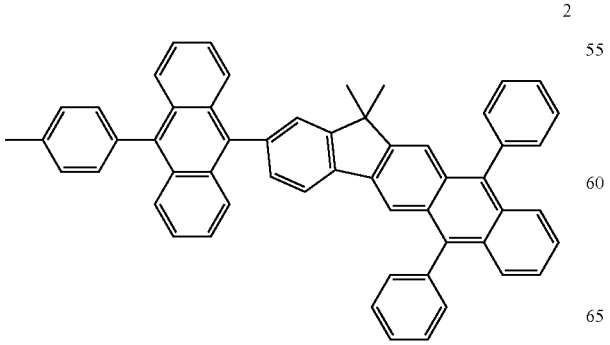
3
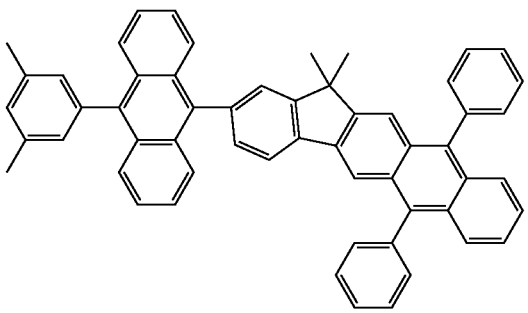
4
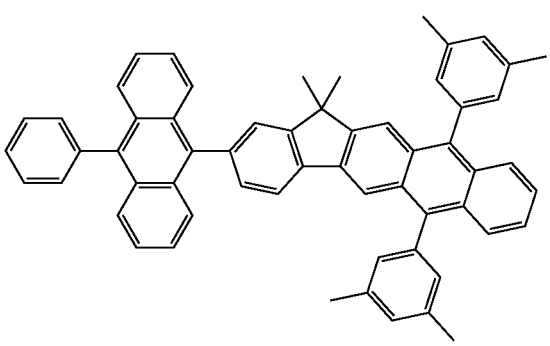
5
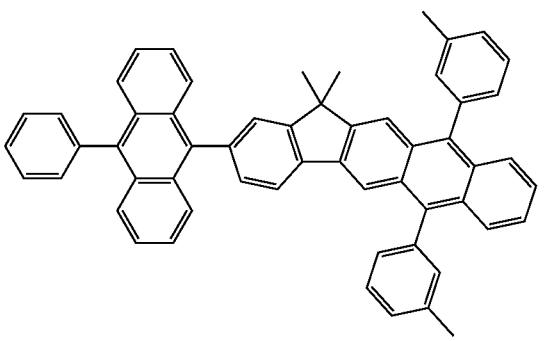
6
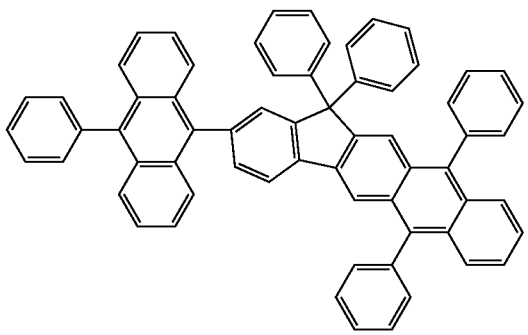

7
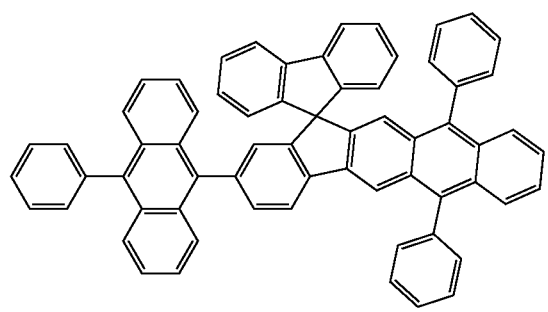

8
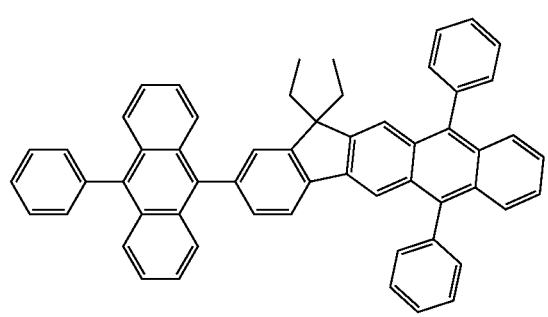

9
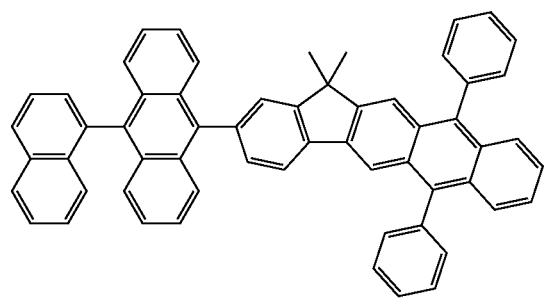

10
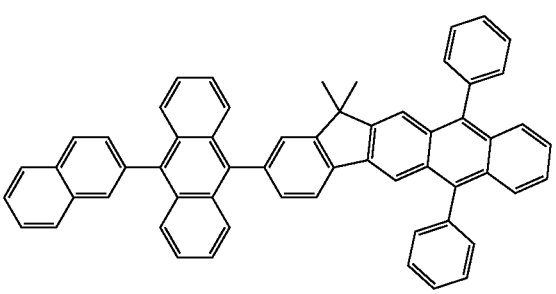

11
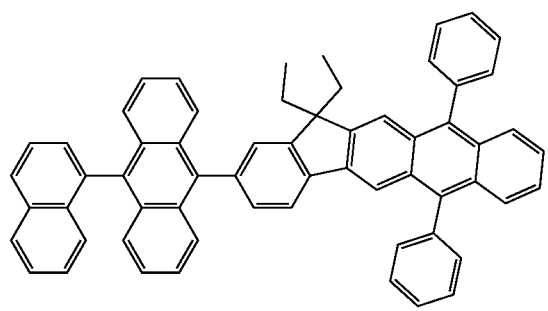

12
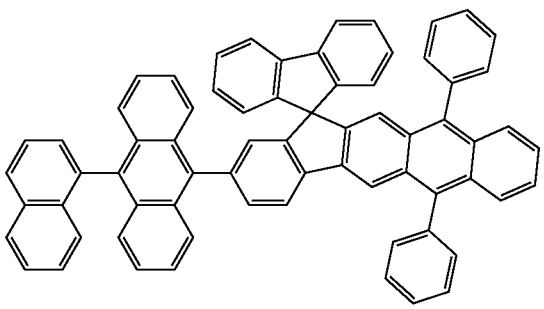

13
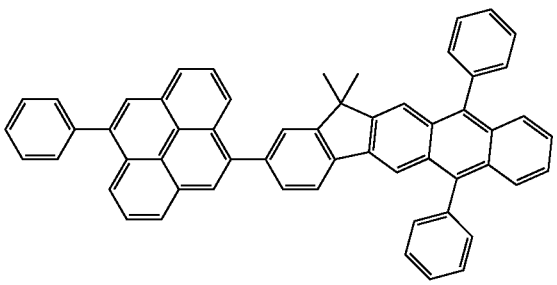

14
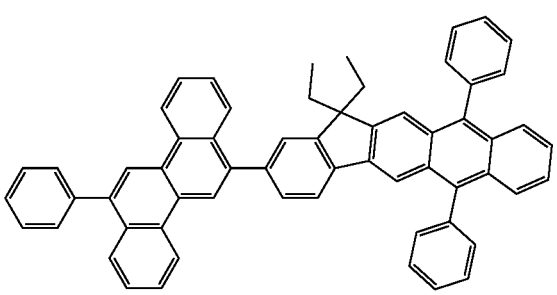

15
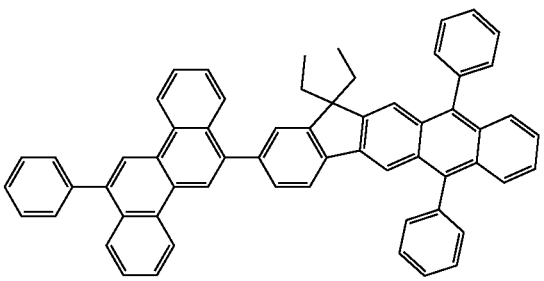

11. The organic light-emitting device as claimed in claim 1, wherein
the first electrode is an anode,
the second electrode is a cathode, and
the organic layer includes:
a hole transport region between the first electrode and the emission layer, the hole transport region including at least one of a hole injection layer, a hole transport layer, a buffer layer, or an electron blocking layer, and
an electron transport region between the emission layer and the second electrode, the electron transport region including at least one selected from a hole blocking layer, an electron transport layer, or an electron injection layer.

12. The organic light-emitting device as claimed in claim 1, wherein the emission layer further includes a dopant.

* * * * *